United States Patent
Gittes

(10) Patent No.: US 11,071,550 B2
(45) Date of Patent: Jul. 27, 2021

(54) METHODS AND DEVICES FOR TREATING PANCREATITIS

(71) Applicant: UNIVERSITY OF PITTSBURGH—OF THE COMMONWEALTH SYSTEM OF HIGHER EDUCATION, Pittsburgh, PA (US)

(72) Inventor: George K. Gittes, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 86 days.

(21) Appl. No.: 16/620,240

(22) PCT Filed: Jun. 5, 2018

(86) PCT No.: PCT/US2018/035985
§ 371 (c)(1),
(2) Date: Dec. 6, 2019

(87) PCT Pub. No.: WO2018/226643
PCT Pub. Date: Dec. 13, 2018

(65) Prior Publication Data
US 2020/0214715 A1    Jul. 9, 2020

Related U.S. Application Data

(60) Provisional application No. 62/517,342, filed on Jun. 9, 2017.

(51) Int. Cl.
*A61B 17/12* (2006.01)
*A61K 31/05* (2006.01)
(Continued)

(52) U.S. Cl.
CPC .. *A61B 17/12136* (2013.01); *A61B 17/12013* (2013.01); *A61B 17/12099* (2013.01);
(Continued)

(58) Field of Classification Search
CPC ........ A61B 17/12136; A61B 17/12013; A61B 17/12099; A61B 2017/00318;
(Continued)

(56) References Cited

U.S. PATENT DOCUMENTS 5,746,717 A    5/1998  Aigner
5,843,028 A   12/1998  Weaver et al.
(Continued)

OTHER PUBLICATIONS

International Search Report and Written Opinion dated Sep. 25, 2018, from International Application No. PCT/US2018/035985, 11 pages.

(Continued)

*Primary Examiner* — Katrina M Stransky
*Assistant Examiner* — Paige A Codrington
(74) *Attorney, Agent, or Firm* — Meunier Carlin & Curfman LLC

(57) ABSTRACT

Disclosed herein are methods and devices for treating pancreatitis. In the methods described herein, the distal portion of a catheter is routed into the pancreatic duct. The catheter delivers to the pancreatic duct an effective amount of a composition at an effective infusion pressure, wherein the amount and infusion pressure of the composition are effective to decrease the secretion of digestive enzymes from one or more exocrine tissues of the pancreas. The reduction of digestive enzymes may reduce damage to the islet cells typically seen in chronic pancreatitis. Backflow of the composition out of the pancreatic duct is limited, for example, by an occluding system, and aspiration system, or both.

20 Claims, 15 Drawing Sheets

(51) Int. Cl.
  *A61K 31/19* (2006.01)
  *A61B 17/00* (2006.01)
(52) U.S. Cl.
  CPC .............. *A61K 31/05* (2013.01); *A61K 31/19* (2013.01); *A61B 2017/0034* (2013.01); *A61B 2017/00318* (2013.01); *A61B 2017/00469* (2013.01); *A61B 2017/00818* (2013.01); *A61B 2017/00898* (2013.01); *A61B 2217/005* (2013.01)
(58) Field of Classification Search
  CPC .. A61B 2017/0034; A61B 2017/00469; A61B 2017/00818; A61B 2017/00898; A61B 2217/005; A61B 1/00177; A61B 1/05; A61B 1/0615; A61B 1/00098; A61B 17/12159; A61B 17/12172; A61B 17/12177; A61B 2017/00876; A61B 17/12131; A61K 31/05; A61K 31/19
  USPC ........................................................ 606/194
  See application file for complete search history.

(56) References Cited

U.S. PATENT DOCUMENTS

| | | | | |
|---|---|---|---|---|
| 5,904,670 | A * | 5/1999 | Schreiner | A61M 25/0084 604/523 |
| 6,699,231 | B1 * | 3/2004 | Sterman | A61B 17/12045 604/509 |
| 8,808,270 | B2 * | 8/2014 | Dann | A61M 25/09041 604/514 |
| 2010/0174139 | A1 * | 7/2010 | Windheuser | A61M 25/09041 600/106 |
| 2013/0324926 | A1 * | 12/2013 | Nelson | A61F 5/0036 604/115 |
| 2015/0133780 | A1 | 5/2015 | Kipshidze et al. | |

OTHER PUBLICATIONS

Barresi, L., et al. "Endoscopic ultrasound-guided ethanol ablation of pancreatic remnant following complicated total pancreatectomy." Endoscopy 45.S 02 (2013): E195-E196.
Bellin MD, et al.,Total pancreatectomy and islet autotransplantation in chronic pancreatitis: recommendations from PancreasFest. Pancreatology. Jan.-Feb. 2014;14(1):27-35.
Boerma D, Straatsburg IH, Offerhaus GJ, Gouma DJ, van Gulik TM. Experimental model of obstructive, chronic pancreatitis in pigs. Dig Surg. 2003;20(6):520-526.
Bridges N. Diabetes in cystic fibrosis. Paediatr Respir Rev. May 2013;14 Suppl 1:16-8.
Delaune V, Berney T, Lacotte S, Toso C. Intraportal islet transplantation: the impact of the liver micro-environment. Transpl Int. Jan. 21, 2017.
DiMaio, et al., Ablation of Pancreatic Cystic Lesions the Use of Multiple Endoscopic UltrasoundYGuided Ethanol Lavage Sessions, Pancreas & vol. 40, No. 5, Jul. 2011, 664-668.
Gibly RF, Zhang X, Graham ML, et al. Extrahepatic islet transplantation with microporous polymer scaffolds in syngeneic mouse and allogeneic porcine models. Biomaterials. 2011;32(36):9677-9684.
Hafezi-Nejad N, Singh VK, Johnson SI, Makary MA, Hirose K, Fishman EK, Zaheer A. Surgical approaches to chronic pancreatitis: indications and imaging findings.Abdom Radiol (NY). Oct. 2016;41(10):1980-96.
Kelly A, Moran A.Update on cystic fibrosis-related diabetes. J Cyst Fibros. Jul. 2013;12(4):318-31.
Lévy P, Domínguez-Muñoz E, Imrie C, Löhr M, Maisonneuve P. Epidemiology of chronic pancreatitis: burden of the disease and consequences. United European Gastroenterol J. Oct. 2014;2(5):345-54.

Lowenfels AB, Maisonneuve P, Lankisch PG. Chronic pancreatitis and other risk factors for pancreatic cancer. Gastroenterol Clin North Am. 1999;28(3):673-685.
Marc Giovannini, MD, Editorial: Concentration-dependent ablation of pancreatic tissue by EUS-guided ethanol injection, (2007) 278-280.
Matthes, Kai, et al. Concentration-dependent ablation of pancreatic tissue by EUS-guided ethanol injection. Gastrointestinal endoscopy 65.2 (2007): 272-277.
Ode KL, Moran A. New insights into cystic fibrosis-related diabetes in children. Lancet Diabetes Endocrinol. 2013;1(1):52-58.
Pan FC, Bankaitis ED, Boyer D, et al. Spatiotemporal patterns of multipotentiality in Ptf1a-expressing cells during pancreas organogenesis and injury-induced facultative restoration. Development. 2013;140(4):751-764.
Raimondi S, Lowenfels AB, Morselli-Labate AM, Maisonneuve P, Pezzilli R. Pancreatic cancer in chronic pancreatitis; aetiology, incidence, and early detection. Best Pract Res Clin Gastroenterol. 2010;24(3):349-358.
Riff BP, Chandrasekhara V. The Role of Endoscopic Retrograde Cholangiopancreatography in Management of Pancreatic Diseases. Gastroenterol Clin North Am. Mar. 2016;45(1):45-65.
Saisho Y, Butler AE, Manesso E, Galasso R, Zhang L, Gurlo T, Toffolo GM, Cobelli C, Kavanagh K, Wagner JD, Butler PC. Relationship between fractional pancreatic beta cell area and fasting plasma glucose concentration in monkeys. Diabetologia. Jan. 2010;53(1):111-4.
Song Z, Fusco J, Zimmerman R, Fischbach S, Chen C, Ricks DM, Prasadan K, Shiota C, Xiao X, Gittes GK. Epidermal Growth Factor Receptor Signaling Regulates β Cell Proliferation in Adult Mice. J Biol Chem. Oct. 21, 2016;291(43):22630-22637.
Stram M, Liu S, Singhi AD. Chronic Pancreatitis. Surg Pathol Clin., Dec. 2016;9(4):643-659.
Tanaka T, Ichiba Y, Fujii Y, Itoh H, Kodama O, Dohi K. New canine model of chronic pancreatitis due to chronic ischemia with incomplete pancreatic duct obstruction. Digestion. 1988;41(3):149-155.
Uc A, Andersen DK, Bellin MD, Bruce JI, Drewes AM, Engelhardt JF, Forsmark CE, Lerch MM, Lowe ME, Neuschwander-Tetri BA, O'Keefe SJ, Palermo TM, Pasricha P, Saluja AK, Singh VK, Szigethy EM, Whitcomb DC, Yadav D, Conwell DL.Chronic Pancreatitis in the 21st Century—Research Challenges and Opportunities: Summary of a National Institute of Diabetes and Digestive and Kidney Diseases Workshop. Pancreas. Nov. 2016;45(10):1365-1375.
Wiersema MJ, Wiersema LM. Endosonography-guided celiac plexus neurolysis. Gastrointest Endosc. 1996;44(6):656-662.
Xiao X, Chen Z, Shiota C, et al. No evidence for beta cell neogenesis in murine adult pancreas. J Clin Invest. 2013;123(5):2207-2217.
Xiao X, Gaffar I, Guo P, et al. M2 macrophages promote beta-cell proliferation by upregulation of SMAD7. Proc Natl Acad Sci U S A. 2014;111(13):E1211-1220.
Xiao X, Guo P, Chen Z, et al. Hypoglycemia reduces vascular endothelial growth factor A production by pancreatic beta cells as a regulator of beta cell mass. J Biol Chem. 2013;288(12):8636-8646.
Xiao X, Guo P, Prasadan K, Shiota C, Peirish L, Fischbach S, Song Z, Gaffar I, Wiersch J, El-Gohary Y, Husain SZ, Gittes GK. Pancreatic cell tracing, lineage tagging and targeted genetic manipulations in multiple cell types using pancreatic ductal infusion of adeno-associated viral vectors and/or cell-tagging dyes. Nat Protoc. Dec. 2014;9(12):2719-24.
Xiao X, Guo P, Shiota C, et al. Neurogenin3 activation is not sufficient to direct duct-to-beta cell transdifferentiation in the adult pancreas. J Biol Chem. 2013;288(35):25297-25308.
Xiao X, Prasadan K, Guo P, et al. Pancreatic duct cells as a source of VEGF in mice. Diabetologia. 2014;57(5):991-1000.
Xiao X, Wiersch J, El-Gohary Y, et at TGFbeta receptor signaling is essential for inflammation-induced but not beta-cell workload-induced beta-cell proliferation. Diabetes. 2013;62(4):1217-1226.
Yadav D, Lowenfels AB. The epidemiology of pancreatitis and pancreatic cancer. Gastroenterology. Jun. 2013;144(6):1252-61. doi: 10.1053/j.gastro.2013.01.068. Review.

(56) References Cited

OTHER PUBLICATIONS

Yadav D, Timmons L, Benson JT, Dierkhising RA, Chari ST., Incidence, prevalence, and survival of chronic pancreatitis: a population-based study. Am J Gastroenterol. Dec. 2011;106(12):2192-9.

* cited by examiner

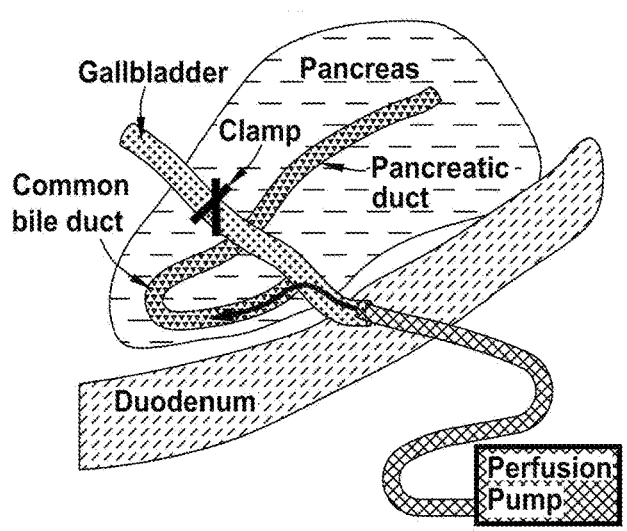
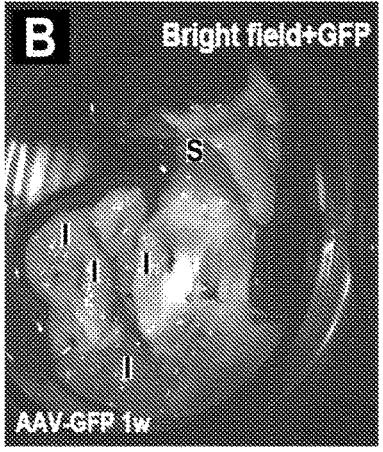
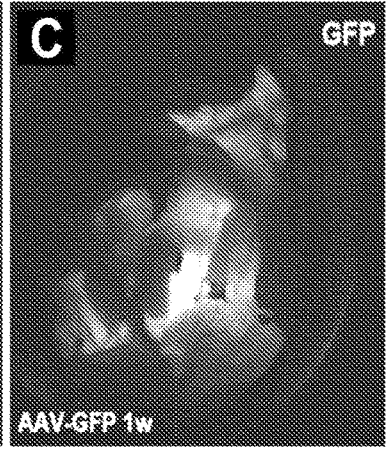
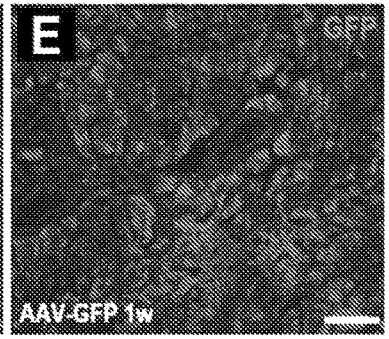
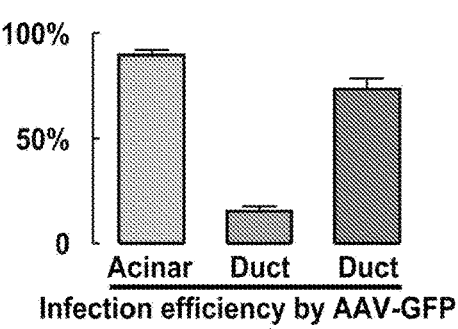
FIG. 1A-F

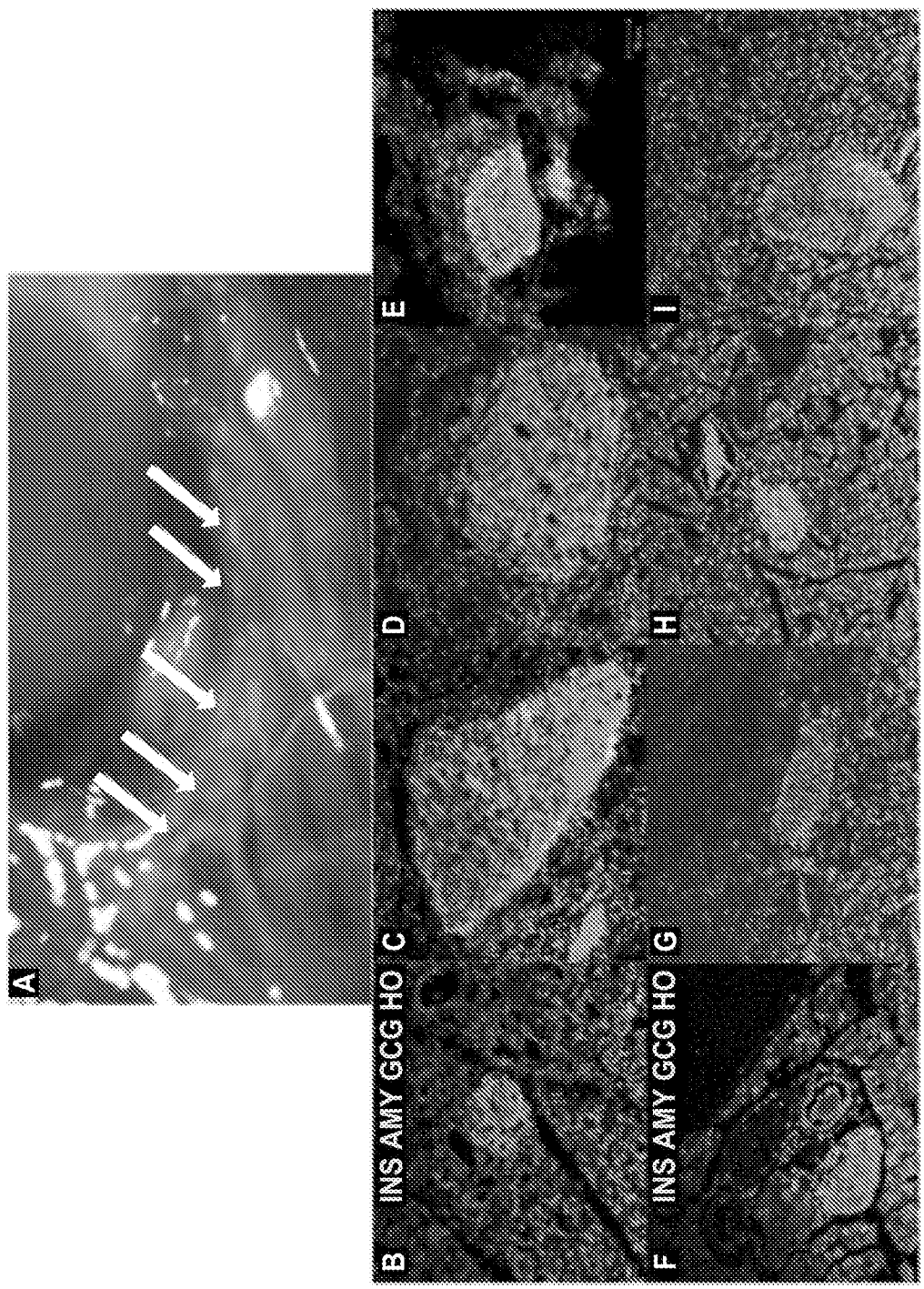
FIG. 2A-O

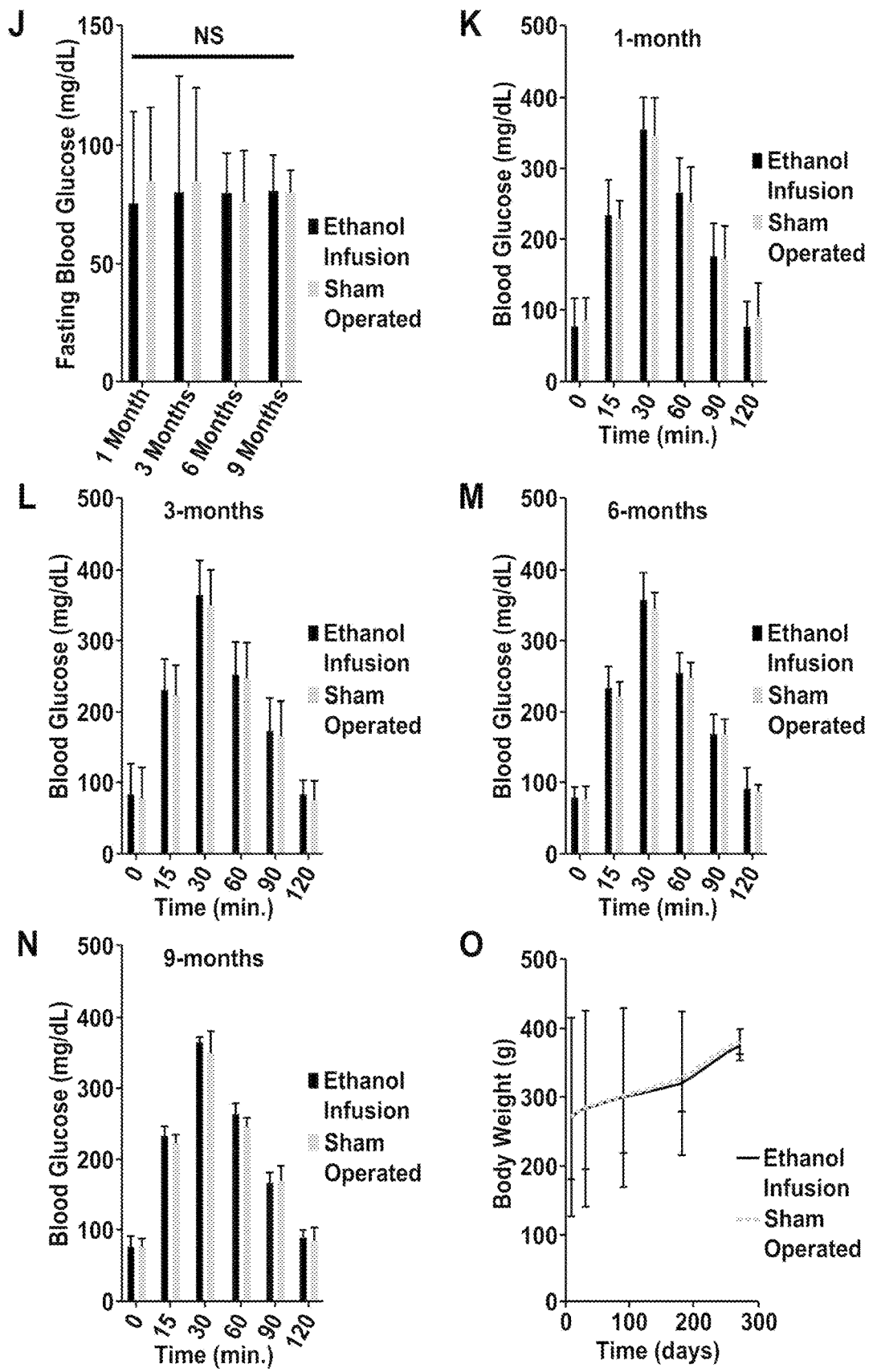
FIG. 2A-O Cont.

METHODS AND DEVICES FOR TREATING PANCREATITIS

RELATED APPLICATIONS

This application is a national stage application filed under 35 U.S.C. § 371 of PCT/US2018/035985, filed Jun. 5, 2018, which claims the benefit of U.S. Provisional Application No. 62/517,342, filed Jun. 9, 2017, which is incorporated by reference in its entirety for all purposes.

FIELD

The field of the invention is the treatment of chronic pancreatitis.

BACKGROUND

Chronic pancreatitis is a substantial clinical problem in the United States and around the world (1, 2), affecting some 140,000 individuals in the United States. Therapeutic interventions for chronic pancreatitis typically involve invasive and morbid surgical procedures. Chronic pancreatitis involves severe chronic pain due to progressive inflammatory changes that result in permanent destruction of initially the exocrine pancreas, and later the endocrine pancreas. The tissue destruction and pain are thought to be due to intrapancreatic activation of digestive acinar enzymes. The pain is generally treated by long-term use of narcotics. Loss of exocrine pancreatic digestive enzymes also leads to malabsorption, so patients must also take enzyme replacements (pancrelipase, or CREON) for life.

Chronic pancreatitis has potentially life-threatening complications such as pseudocyst, pancreatic ascites, biliary obstruction, and a 13-fold increase in risk of exocrine pancreatic cancer (13). The exocrine damage causes an ongoing release of intracellular acinar enzymes and lysosomal contents, creating a toxic milieu for the otherwise healthy insulin-producing islet cells. This leads to both islet loss and to islet cell dysfunction. In addition, again likely due to the toxic milieu, the function of the beta cells in terms of glucose sensing and insulin release is also adversely affected (3). Due to these effects, most subjects also go on to develop insulinopenia and diabetes mellitus, which frequently requires insulin therapy.

Along similar lines, over the last few decades subjects with cystic fibrosis have been experiencing increasing life expectancy (4). Concomitant with that, and presumably also due to the same toxic milieu caused by exocrine pancreas dysfunction, many cystic fibrosis subjects (20% of adolescents and 50% of adults) go on to develop insulinopenia and cystic fibrosis related diabetes (CFRD). CFRD is the most common co-morbidity of cystic fibrosis (5). The methods and devices described herein for treating chronic pancreatitis may also be useful for these cystic fibrosis patients.

Current therapy for chronic pancreatitis is fairly limited. For example, non-surgical treatment is essentially restricted to only pain control and enzyme replacement, without addressing the other major risks and morbidities enumerated above (6). For example, surgery consists of either improved drainage of dilated, blocked pancreatic ducts (only applicable in selected subjects with amenable anatomy), or else surgical removal of part or all of the pancreas (7).

One therapeutic approach for subjects that are not yet diabetic is a total pancreatectomy with islet auto transplantation (TPIAT, 8). In this procedure, the pancreas is removed, the islets are harvested, and the islets are then transplanted back into the subject, for example, to the liver. The surgical removal of pancreatic tissue effected by chronic pancreatitis is the most reliable way to directly cure or prevent most of the problems associated with chronic pancreatitis, including chronic pain, cancer risk, and complications. However, removal of pancreatic tissue will not only exacerbate the need for supplemental enzymes, but also will enhance the risk of diabetes mellitus. Even with TPIAT, the yield of islets from the removed pancreas after digestion and islet isolation for auto transplantation of the islets is relatively low, and the hepatic location for islets has been well shown to be sub-optimal for islet function for several reasons (9). First, the transplanted islets lack the native pancreatic vasculature, which provided a perfect alignment of the specialized islet capillaries with each individual beta cell. These specialized capillaries are fenestrated and specifically optimal for glucose sensing by beta cells. In addition, it is important that the beta cell is in immediate apposition to the capillaries. If not, it creates a significant increase in the diffusion distance between the beta cell and the blood stream for both glucose (toward the beta cell and away from the capillaries) and for insulin (out of the beta cell and toward the capillary). This increased diffusion distance creates a time lag for both glucose sensing and insulin delivery, which can have significant deleterious effects.

SUMMARY

Disclosed herein are methods and devices for treating pancreatitis. A catheter is routed into the pancreatic duct and delivers an effective amount of a composition at an effective infusion pressure. The composition is effective to decrease the secretion of digestive enzymes from one or more exocrine tissues of the pancreas, which may reduce damage to the islet cells typically seen in chronic pancreatitis. Backflow of the composition from the pancreatic duct is limited, for example, by an occluding system, and aspiration system, or both.

Certain embodiments of the method for treating pancreatitis can include advancing a distal portion of the catheter through an ampulla of Vater and into a pancreatic duct of the subject (over a guidewire, for example). A steering wire can be attached to the distal portion of the catheter, such that creating tension in the steering steers the catheter into the pancreatic duct. The catheter can be used with an endoscope that is advanced through the esophagus, stomach, and duodenum of the subject prior to advancing the catheter through the ampulla of Vater. In some embodiments, the pancreatic duct is infused with a contrast fluid to visualize the location of the catheter.

In some embodiments, the composition can include ethanol in a concentration of from 40% to 70%. In some embodiments, the composition can include acetic acid in a concentration of from 0.1% to 5%. The effective amount of the composition can be anywhere from 3 to 50 milliliters. The effective infusion pressure can be anywhere from 100 to 2000 centimeters of water, and can be modulated while the catheter is in the pancreatic duct. In some embodiments, backflow out of the pancreatic duct is limited for a dwell time of from 3 to 30 minutes.

As described above, the method includes a step of limiting backflow of the composition out of the pancreatic duct. This can include limiting backflow of the composition into surrounding structures such as a biliary tree, an ampulla of Vater, and/or a duodenum. Backflow can be limited by activating one or both of an occluding system and an aspiration system. An occluding system includes an occluding mechanism and, in some embodiments, an occluding system lumen and/or an occluding system wire. In some embodiments, the occluding system can be activated by pushing a fluid through an occluding system lumen and inflating an occluding mechanism such as a balloon. In some embodiments, the occluding mechanism can be activated, at least in part, by an occluding system wire. Alternatively, or in addition, an occluding mechanism can be activated by increasing the size of a distal portion of the catheter. Alternatively, or in addition, an occluding mechanism can be activated by advancing or retracting a distal portion of a sheath over the catheter to increase its size at a particular location. The occluding mechanism can remain activated for a dwell time of from 3 to 30 minutes, or, in some embodiments, from 5 to 15 minutes.

Some embodiments can include an aspiration system to suction excess fluid from the pancreatic duct (to remove fluid once the dwell time is over, and/or to prevent backflow of fluid out of the pancreatic duct). The aspiration system includes an aspiration port, and aspiration lumen that extends through the catheter (or a sheath extending over the catheter). In some embodiments the aspiration system can include an aspiration element that protrudes away from the catheter and directs fluid into the aspiration port. The aspiration element can be positioned proximally or distally to the occluding mechanism. In some embodiments, the aspiration system is activated by creating a negative pressure in an aspiration lumen of the catheter to draw fluid into the aspiration port.

Devices for treating pancreatitis are also disclosed herein. The devices include a catheter sized and configured for placement in a human pancreatic duct. For example, the outer diameter of the catheter can be from 3 to 10 French. The device further includes an occluding system, an aspiration system, or both. The occluding system can include an occluding mechanism positioned positioned less than 50 millimeters from the distal end of the catheter (from 5 to 15 millimeters proximal to the distal end of the catheter, in some embodiments). The aspiration system can include an aspiration port positioned less than 50 millimeters from the distal end of the catheter (from 5 to 15 millimeters proximal to the distal end of the catheter, in some embodiments). The catheter includes at least two lumens extending therethrough for serving various functions of the catheter.

In some embodiments, the occluding mechanism can include a balloon in fluid communication with an occluding system lumen that extends through the catheter. Alternatively, or in addition, the occluding mechanism can include a distal portion of a sheath that extends partially or fully over the catheter. The distal portion of the sheath can be bulbous or tapered, or can be a collapsible cup or funnel, and is meant to increase the outer diameter of the catheter to block the pancreatic duct. In some embodiments, a wire can be attached to the distal portion of the sheath, such that creating tension in the wire causes the distal portion of the sheath to retract backward into an accordion-like structure that acts as an occluding mechanism. In some embodiments, the occluding mechanism can include a swelling material positioned within or on the surface of the catheter.

The catheter can include multiple lumens serving different functions. For example, the catheter includes an infusion lumen, and can include a lumen associated with the occluding system. The catheter can include a lumen associated with the aspiration system, with the delivery of the contrast fluid, and/or a lumen for routing the guidewire or steering wire through the catheter or sheath. One lumen can serve multiple functions, or each function can be performed using a separate lumen.

BRIEF DESCRIPTION OF THE DRAWINGS

FIGS. 1A-1F show the results of pancreatic infusion with green fluorescent protein (GFP). (A) Schematic of the infusion model. (B-D) Retrograde infusion was performed with an adeno-associated virus serotype 8 (AAV) carrying a GFP expression sequence (AAV-GFP). One week after infection, the pancreas was broadly infected, as shown by the gross images (B and C) and by pancreatic sections (D and E) for GFP. Ductal cells are labeled with Dolichus Biflorus Agglutinin (DBA), and cell nuclei are labeled with Hoechst (HO). (F) Quantification of infection efficiency 1 week after infusion of virus. S: spleen; I: intestine. Scale bar is 50 micrometers.

FIGS. 2A-2O show the results of mouse pancreatic duct infusion with 100% ethanol at various time points after infusion. Post ethanol infusion pancreas at (A) 6-months showing preserved white islets (arrows). Amylase (AMY) staining is absent at all time points in ethanol-infused pancreas, but insulin (INS) positive β-cells and glucagon (GCG) positive α-cells persist (B: 1 month, C: 3 months, D: 6 months, E: 9 months). (F-I) Sham operated controls show intact islets and AMY-positive acinar tissue (F: 1 month, G: 3 months, H: 6 months, I: 9 months). HO: Hoescht nuclear stain, scale bar is 50 microns (J) Fasting blood glucose shows no difference at multiple time points after ethanol infusion compared to sham-operated mice. (K-N) There was no difference in glucose tolerance testing between ethanol-infused mice as compared to sham-operated at all time points. (O) The ethanol-infused and sham-operated mice gained weight at a similar rate, with both groups on an elemental diet.

FIG. 12A shows a catheter in the pancreatic duct (tip of catheter shown by the arrow) and a clamp on the bile duct (arrowhead), and FIG. 12B shows the same shot after infusion of a contrast dye into the pancreatic duct and secondary ducts (arrows).

FIG. 17A shows the cup shaped distal portion in a collapsed position. FIG. 17B shows the cup shaped distal portion in an expanded position.

DETAILED DESCRIPTION OF THE INVENTION

Definitions

Figures 3A, 3B, 3C, 3D, 3E:
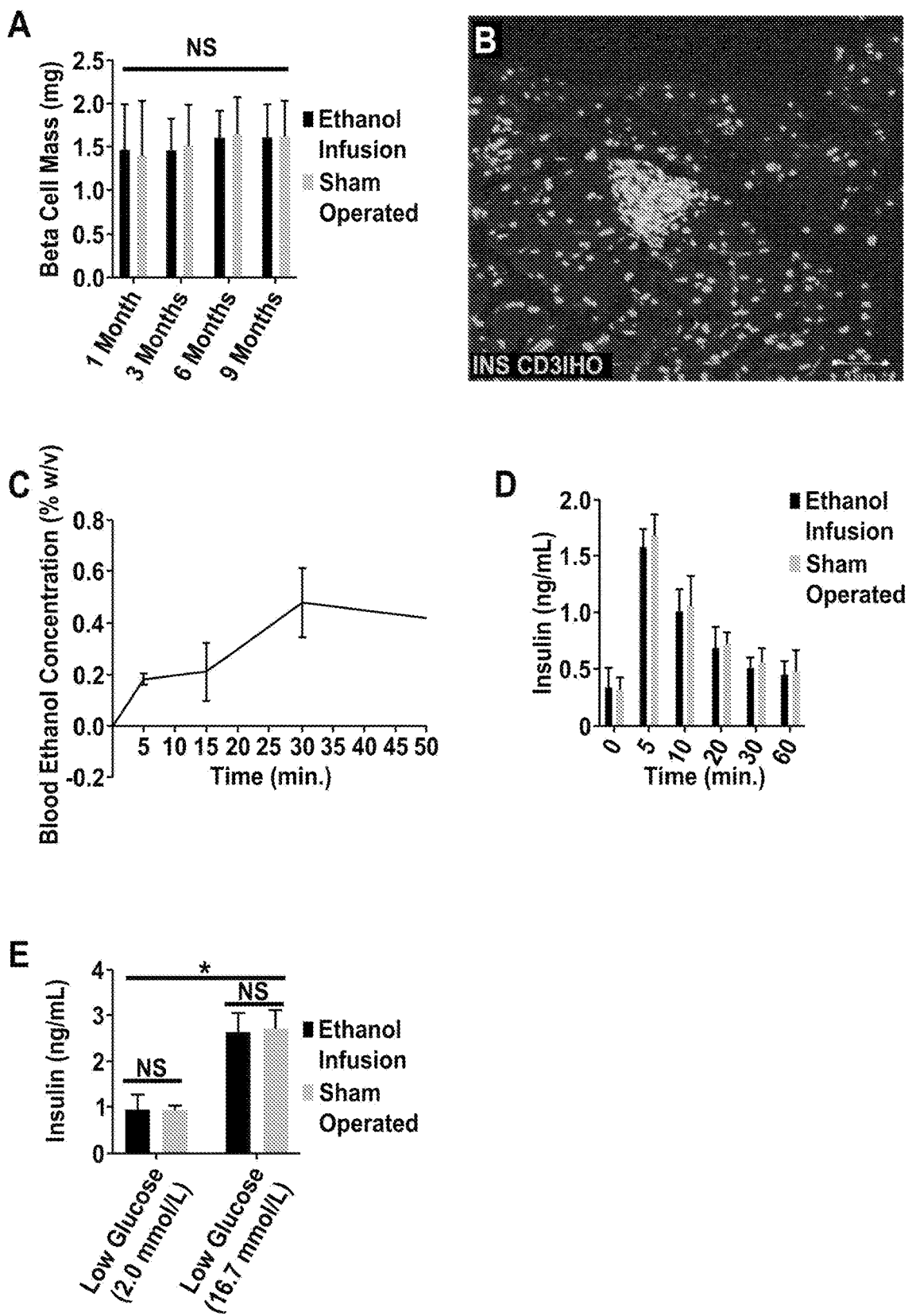
FIGS. 3A-3E show that β-cell mass and endocrine function are preserved after infusion of 100% ethanol. (A) There is no difference in β-cell mass in the pancreatic tail between sham-operated and ethanol-infused mice across all time points, suggesting preservation of islets. (B) Blood vessels (CD31 staining), including islet vessels are maintained after ethanol infusion at 9 months. scale bar is 50 micrometers (C) Blood ethanol levels rise quickly after pancreatic ductal ethanol infusion. (D) In vivo and (E) in vitro glucose stimulated insulin secretion (GSIS) show no difference between sham-operated and ethanol-infused mice/islets at the 9-month time point.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, "distal" and "distally" refer to a direction away, or farther from, a practitioner performing a procedure. "Proximal" and "proximally" refer to a direction towards, or closer to, a practitioner performing a procedure. For example, an element that is located "proximal to the distal end" of a device is located closer to the practitioner than the distal end of the same device when the device be lengthened to its fullest extent.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of pancreatitis), during early onset (e.g., upon initial signs and symptoms of pancreatitis), or after an established development of pancreatitis. Prophylactic administration can occur for several days to years prior to the manifestation of symptoms of pancreatitis.

The terms "prevent," "preventing," "prevention," and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms. For example, the infusion of ethanol or acetic acid into the pancreatic duct of a subject with pancreatitis may prevent chronic pancreatitis related diabetes.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

An "effective amount" is an amount sufficient to effect beneficial or desired results. An effective amount can be administered in one or more administrations, applications or dosages. For example, a subject can be treated with an effective amount of a composition to decrease the secretion of digestive enzymes from one or more exocrine tissues of the pancreas.

To "ablate" means to reduce the functionality. For example, treatment with the compositions disclosed herein ablate one or more exocrine tissues of the pancreas, meaning that it decreases the secretion of digestive enzymes from one or more exocrine tissues of the pancreas.

The term "ablate" and grammatical variations thereof as used herein can indicate a partial reduction in functionality or a total reduction in functionality.

"Pancreatitis" refers to a condition of inflammation within the pancreas. "Chronic pancreatitis" refers to pancreatic inflammation over long durations of time. In some embodiments, the inflammation over long durations is continuous.

The term "exocrine tissue" indicates tissue that produces and secretes substances onto an epithelial surface by way of a duct. In the pancreas, the exocrine tissue is tissue that secretes digestive enzymes to be delivered to the gastrointestinal tract via the pancreatic duct. The cells of the exocrine pancreatic tissue include acinar cells, which produce and secrete digestive enzymes, and duct cells, which produce and secrete bicarbonate.

As used herein, "pancreatic duct" refers to the main or major pancreatic duct, which is also known as the duct of Wirsung. The pancreatic duct joins the common bile duct just prior to the ampulla of Vater, after which both ducts perforate the medial side of the second portion of the duodenum at the major duodenal papilla.

DETAILED DESCRIPTION

Disclosed herein are methods and devices for treating pancreatitis. In the methods described herein, the distal portion of a catheter is routed into the pancreatic duct of a subject. The catheter delivers to the pancreatic duct an effective amount of a composition at an effective infusion pressure, amount, and concentration, to decrease the secretion of digestive enzymes from one or more exocrine tissues of the pancreas. The reduction of digestive enzymes may reduce damage to the islet cells typically seen in chronic pancreatitis. In some embodiments, the composition comprises ethanol, acetic acid, or a mixture thereof.

Backflow of the composition out of the pancreatic duct is limited, for example, by an occluding system, an aspiration system, or both. The occluding system includes an occluding mechanism and, in some embodiments, an occluding system lumen and/or an occluding system wire that extends longitudinally through or along the catheter to the occluding mechanism.

Example occluding mechanisms 36a, 36b, 36c, and 36d are shown in FIGS. 15-19 and are described in Example 5, below. The occluding mechanism 36 is positioned at or near the distal end of the catheter 33. The occluding mechanism 36 has an outer diameter that is wider than the outer diameter of the catheter 33, such that it contacts the walls of the pancreatic duct to physically block fluid exiting the catheter (for example, from port 32) from moving past it in a proximal direction. As such, the occluding mechanism is a means for preventing proximal flow of infused fluid with respect to the catheter. Depending upon the type of occluding mechanism used, an occluding system lumen can be provided to communicate with the occluding mechanism. For example, in the embodiment shown in FIGS. 15 and 19, the occluding mechanism 36a is a balloon and the occluding system lumen 41 extends through the catheter 33 to provide inflation fluid to the balloon 36a.

If an aspiration system is included, the aspiration system includes an aspiration port that is in communication with an aspiration lumen. The aspiration system can also include an aspiration element that protrudes outwardly from the catheter, or from a sheath that extends at least partially over the catheter. The aspiration element directs aspirated fluid into the aspiration port and the aspiration lumen. The aspiration lumen extends through the catheter, or, in some embodiments, through the sheath extends at least partially over the catheter. The aspiration port and aspiration element can be positioned proximally or distally to the occluding mechanism, or, in some embodiments, the aspiration port and aspiration element is positioned on the occluding mechanism.

In some embodiments, the catheter is advanced through the ampulla of Vater and into the pancreatic duct. The catheter can be configured to be used in conjunction with an endoscope. In some embodiments, the methods include advancing an endoscope through an esophagus, stomach, and duodenum and advancing the catheter out a distal port of the endoscope and through the ampulla of Vater, for example, as part of an endoscopic retrograde cholangiopancreatographic (ERCP) procedure. In some embodiments, a guidewire can be advanced into the pancreatic duct prior to the catheter, and the catheter can be advanced over the guidewire. Alternatively, or in addition to a guidewire, a steering wire could attach to a distal portion of the catheter, and tension can be created in the steering wire to pull the distal portion of the catheter in a specific direction, such that the distal portion of the catheter is steered toward and/or into the pancreatic duct.

The amount of the composition that is delivered into the pancreatic duct can be, for example, from 3 to 50 milliliters, including from 10 to 50 milliliters, from 20 to 50 milliliters, from 30 to 50 milliliters, or from 40 to 50 milliliters. In some embodiments, the amount of the composition that is delivered into the pancreatic duct is 35, 40, 45, or 50 milliliters.

While the examples disclosed herein discuss compositions comprising ethanol or acetic acid for ablation of the pancreatic exocrine tissue, other compositions might comprise other substances for ablation of the pancreatic exocrine tissue. For example, an effective amount of a composition comprising formaldehyde, propyl alcohol, hydrochloric acid, acrolein, chromic acid and/or acetone may also be delivered to the pancreatic duct, in place of or in combination with ethanol and/or acetic acid, at an infusion pressure effective to decrease the secretion of digestive enzymes from one or more exocrine tissues of the pancreas.

In some embodiments, the concentration of ethanol in the composition being delivered into the pancreatic duct can be, for example, from 10% to 100% volume/volume, including from 20% to 90%, from 30% to 80%, from 35% to 75%, from 40% to 70%, from 45% to 65%, or from 50% to 60% volume/volume. In some embodiments, the composition comprises 50%, 51%, 52%, 53%, 54%, 55%, 56%, 57%, 58%, 59%, or 60% ethanol. The percentages are given as percent volume/volume in water.

In some embodiments, the concentration of acetic in the composition being delivered into the pancreatic duct can be, for example, from 0.1% to 5% volume/volume, including from 0.1% to 1%, from 0.5% to 4.5%, from 1% to 4%, from 1% to 3%, from 1% to 2%, from 2% to 5%, from 2% to 4%, from 2% to 3%, from 3% to 5%, or from 4% to 5% volume/volume. In some embodiments, the composition comprises 0.1%, 0.5%, 1%, 1.5%, 2%, 2.5%, or 3% acetic acid. The percentages are given as percent volume/volume in water.

In some embodiments, the composition being delivered into the pancreatic duct can be a mixture of ethanol, acetic acid and/or any other substance that decreases the secretion of digestive enzymes from one or more exocrine tissues of the pancreas. For example, the composition can contain a mixture of from 10 to 95% volume/volume ethanol and from 0.1% to 5% volume/volume acetic acid. However, in some embodiments, a composition containing ethanol is not mixed with acetic acid or any other substances that decrease the secretion of digestive enzymes. In some embodiments, a composition containing acetic acid is not mixed with ethanol or any other substances that decrease the secretion of digestive enzymes.

The infusion pressure can be, for example, from 100 to 2000 centimeters of water, including from 300 to 1700 centimeters of water, from 300 to 1500 centimeters of water, from 300 to 1200 centimeters of water, or from 500 to 1000 centimeters of water. In some embodiments, the infusion pressure can be 300, 400, 500, 600, 700, 800, 900, 1000, 1100, 1200, 1300, or 1400 centimeters of water. In some embodiments, the infusion pressure can be modulated while the catheter is in the pancreatic duct, for example, to change the pressure of the composition as it is being delivered to the pancreatic duct.

The dwell time refers to a period after the infusion during which an occluding mechanism that limits backflow of the composition out of the pancreatic duct is maintained, allowing the composition in the pancreatic duct to be absorbed by the pancreatic tissue. The dwell time can be, for example, from 3 to 30 minutes, including from 5 to 25 minutes, or from 5 to 20 minutes, or from 5 to 15 minutes, including 5 minutes, 6 minutes, 7 minutes, 8 minutes, 9 minutes, 10 minutes, 11 minutes, 12 minutes, 13 minutes, 14 minutes or 15 minutes of dwell time.

In some embodiments, the methods further include infusing a contrast fluid into the pancreatic duct and visualizing the location of the catheter.

In some embodiments, limiting backflow of the composition out of the pancreatic duct includes limiting backflow into the ampulla of Vater, the biliary tree, and/or the duodenum. Limiting backflow of the composition can be achieved by activating an occluding system and/or an aspiration system. In some embodiments, activating the occluding system can include activating an occluding mechanism. Activating the occluding mechanism is achieved by pushing an inflation fluid through a lumen of the catheter to inflate a balloon. The lumen can, in some embodiments, be an occluding mechanism lumen. In other embodiments, activating an occluding mechanism can include increasing the size of a distal portion of the catheter. For example, the distal portion of the catheter can include a swelling material that can be activated to expand when desired, either by an electrical, a magnetic, or a chemical mechanism. Activating the occluding mechanism can include advancing or retracting a distal portion of a sheath over the catheter, where the occluding mechanism is positioned at the distal portion of the sheath. If an aspiration system is used, activating the aspiration system includes creating a negative pressure in an aspiration lumen of the catheter.

Disclosed herein are devices for treating pancreatitis. As mentioned above, the devices include a catheter sized and configured for placement into a human pancreatic duct. The outer diameter of the catheter can be, for example, from 3 to 10 French, including 3, 4, 5, 6, 7, 8, 9, and 10 French.

An occluding mechanism, an aspiration element, or both are positioned less than 50 millimeters from the distal end, including less than 40 millimeters, less than 30 millimeters, or less than 20 millimeters from the distal end of the catheter. For example, in some embodiments, the occluding mechanism, aspiration element, or both are positioned from 5 to 15 millimeters proximal to the distal end of the catheter.

In some embodiments, the occluding mechanism can include a balloon that is in fluid communication with an occluding system lumen that extends through the catheter. In some embodiments, the occluding mechanism can include the distal portion of a sheath that extends partially or fully over the catheter. The distal portion of the sheath can be bulbous or tapered. In some embodiments, the bulbous or tapered distal portion can include an aspiration port that is in fluid communication with an aspiration lumen. The aspiration lumen can extend at least partially longitudinally through the sheath. In some embodiments, the occluding mechanism includes an expandable and collapsible cup or funnel shaped distal portion of the sheath. The expandable and collapsible cup or funnel shaped distal portion can include an aspiration port in fluid communication with an aspiration lumen, which extends at least partially longitudinally through the sheath. In some embodiments, an occluding system wire is attached to the distal portion of the sheath. Creating tension in the occluding system wire causes the distal portion of the sheath to retract backward into an accordion-like structure. The occluding system wire can extend on the outer surface of the sheath, the inner surface of the sheath, or through an occluding mechanism lumen. An occluding mechanism lumen that houses an occluding system wire can, for example, extend longitudinally through the sheath and/or through the catheter. In some embodiments, the occluding mechanism is a swelling material that is positioned within or on the surface of the catheter.

In some embodiments, the occluding mechanism has a collapsed configuration and an expanded (or activated), configuration. In the expanded configuration, the greatest width of the occluding mechanism is from 0.2 to 2.0 centimeters across (as taken perpendicular to the longitudinal axis of the catheter), including from 0.5 to 1.8 centimeters across, from 0.7 to 1.6 centimeters across, from 0.7 to 1.6 centimeters across, from 0.9 to 1.4 centimeters across, and from 1.1 to 1.3 centimeters across.

The devices for treating pancreatitis includes two or more lumens. The catheter can include an infusion lumen and a contrast fluid lumen. In some embodiments, the infusion lumen and the contrast fluid lumen are at least partially coaxial, such that at least a portion of the lumen space is shared. The catheter can also include a wire lumen for routing a guidewire or a steering wire. In some embodiments, the catheter can include an occluding system lumen, an aspiration lumen, or both.

Example 1

Retrograde Infusion of Ethanol in Mouse Pancreatic Duct

In the methods described herein, ethanol is introduced to the mouse pancreas following a procedure that was initially developed for retrograde intraductal infusion of virus for gene therapy purposes (11). In that gene therapy experiment, the pancreatic infusion transfected the tissue with green fluorescent protein (GFP). Results of that study are included here, as FIG. 1, to demonstrate that pancreatic infusion enables complete or nearly complete access to the pancreatic tissue. FIG. 1A is a schematic of the infusion path. FIGS. 1B and 1C are photographs demonstrating that GFP fluoresces throughout the pancreas 1 week after transfection. FIGS. 1D and 1E are immunofluorescence images showing the successful GFP transfection on a microscopic level. FIG. 1F graphs the infection efficiency of various cell types using the pancreatic infusion method.

In a study analyzing the results of pancreatic duct infusion with ethanol, infusion was followed by sacrifice at 1-month, 3-months, 6-months, and 9-months. In this example, the ethanol concentration is 100%. FIG. 2A shows a representative photograph of the treated pancreas tissue 6-months post-treatment. The islets are visible as small white areas (labeled by white arrows). These islets are not normally visible due to the opaque overlying acinar tissue. Upon sacrifice, there is no evidence of pancreatic acinar tissue, but the pancreatic endocrine tissue, including both β-cells and the glucagon-producing alpha cells, is well-preserved. See FIGS. 2B-2E, where amylase (AMY) staining is absent at all time points in ethanol-infused pancreas, but insulin (INS) positive β-cells and glucagon (GCG) positive α-cells persist (B: 1 month, C: 3 months, D: 6 months, E: 9 months). In FIGS. 2F-2I, sham operated controls show intact islets and AMY-positive acinar tissue (F: 1 month, G: 3 months, H: 6 months, I: 9 months).

Fasting glucose levels and glucose tolerance tests show no difference between ethanol infused mice and sham-operated controls at all time points (FIGS. 2J-2N), suggesting that β-cell function remains intact. Body weight of these mice is also not different from controls (FIG. 2O), but an elemental diet is required to avoid malabsorption.

There is also no significant difference in β-cell mass at any time point (FIG. 3A). A possible explanation is that exocrine destruction is due to direct exposure of the exocrine ducts and acini to the ethanol. Further diffusion of ethanol beyond the exocrine pancreas into the stroma of the pancreas and near the islets may be accompanied by dilution of the ethanol by tissue fluids, plus rapid removal of the ethanol by lymphatic and blood flow, thus sparing the islets (FIG. 3B). Significant levels of ethanol are found in the blood within 5 minutes of infusion (FIG. 3C), confirming that the ethanol rapidly exits from the pancreas. In addition to a normal β-cell mass, endocrine function also appears normal, as shown by in vivo measurements of insulin levels during glucose tolerance testing, as well as in vitro glucose-stimulated insulin secretion (GSIS) at the 9-month time point (FIGS. 3D-3E). Consistent with this normal function, the islet vasculature appears to be intact (CD31 staining, FIG. 3B). Taken together, these data show ablation of the exocrine pancreas, without significant loss of β-cell mass or endocrine function.

Figure 4:
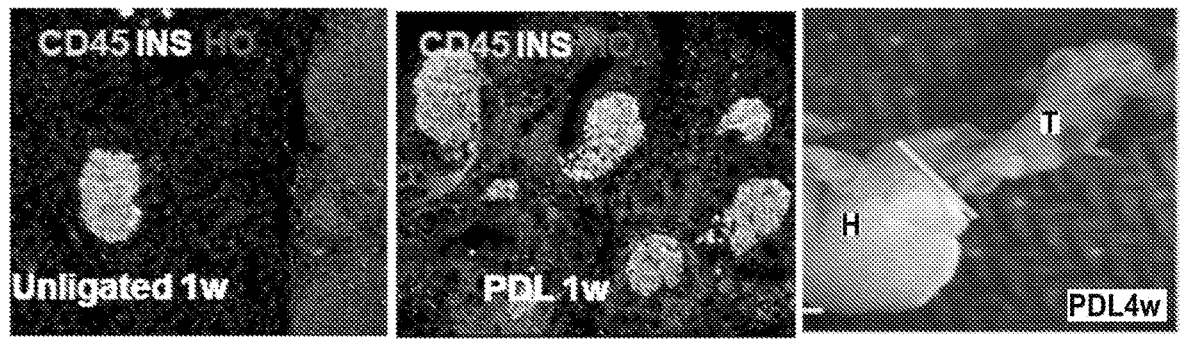
FIG. 4 shows histology one week after pancreatic duct ligation (PDL). Control head of the pancreas (left image) shows normal islets (labeled by insulin antibody staining: Ins) and no CD45+ inflammatory cells (labeled by CD45 antibody staining: CD45). Cell nuclei are labeled with Hoechst (HO). After PDL (center image) there is extensive inflammation (CD45), but islets (Ins) are intact. The image at the right shows the normal head (H) and ligated tail (T) after 4 weeks showing the loss of exocrine tissue, but still white dots of islets in the tail.
Figures 5A, 5B, 5C, 5D, 5E, 5F, 5G, 5H, 5I, 5J:
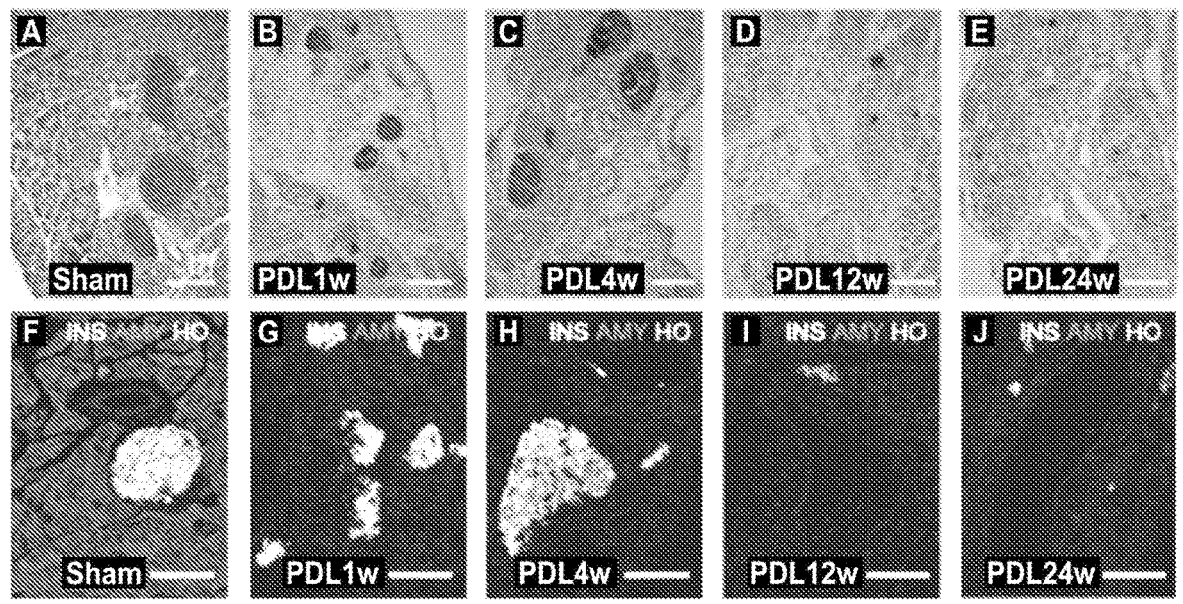
FIGS. 5A-5J are progressive images after PDL that show a loss of islets between week 4 and 12. Ethanol infusion was performed at 8 weeks as an intervention to prevent islet loss. A-E) insulin staining at 0, 1, 4, 12, and 24 weeks after ligation, with islets labeled with DAB for insulin (dark coloring). F-J) Fluorescent immunohistochemistry staining at 0, 1, 4, 12 and 24 weeks after ligation, with islets labeled with insulin (Ins), acinar cells labeled with amylase (Amy), and cell nuclei labeled with Hoechst (HO).
Figures 6A, 6B, 6C, 6D, 6E, 6F, 6G, 6H:
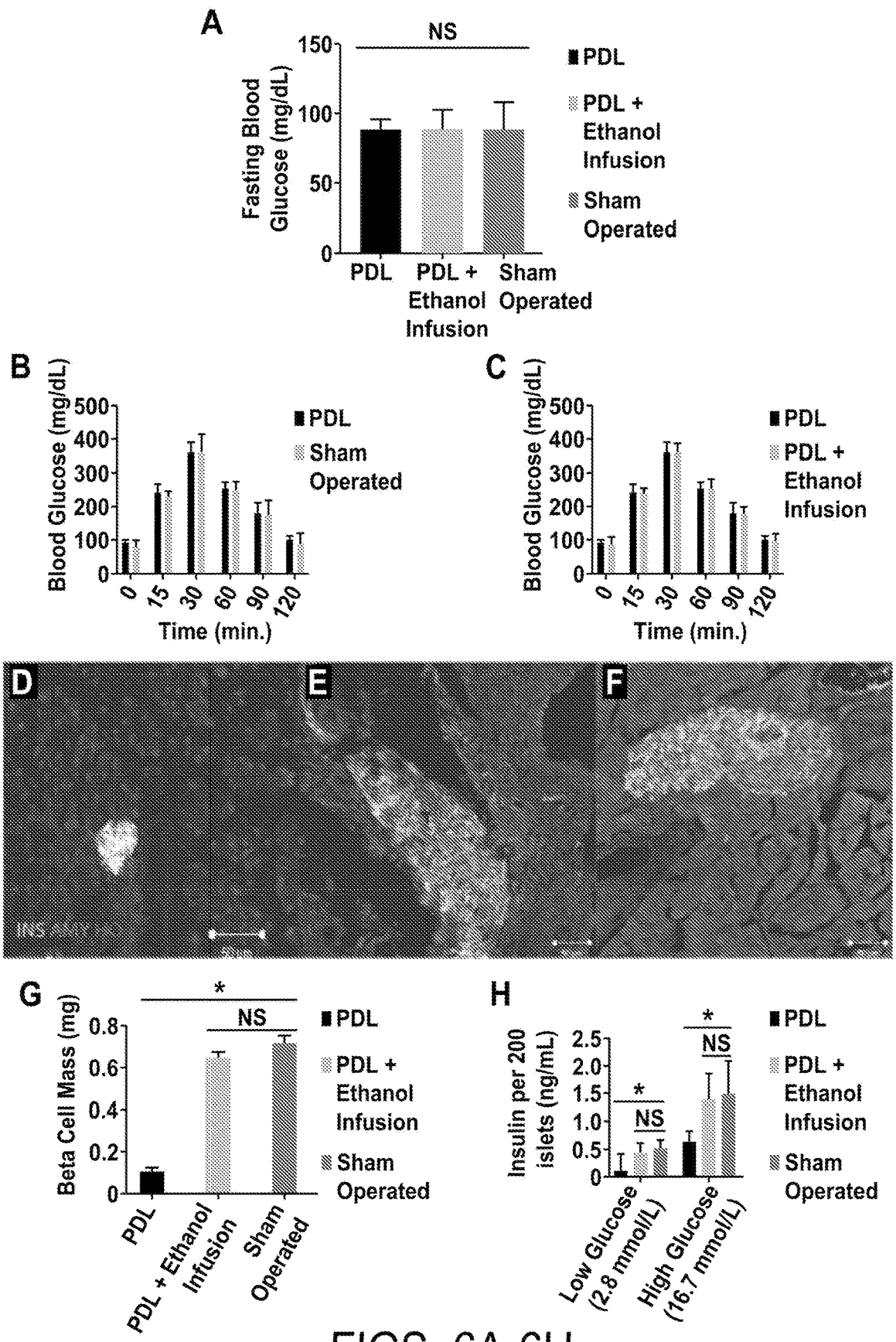
FIGS. 6A-6H show the data gathered following PDL, reflecting the persistence of the islet tissue with ethanol infusion. (A-C) Fasting blood glucose levels and glucose tolerance testing are no different among PDL, PDL+ethanol-infused, and sham operated mice at 24-weeks, likely due to the normal islets in the unligated head of the pancreas. (D) In the ligated tail pancreas, no regeneration of exocrine tissue is seen in the PDL model at 24 weeks. There are also very few islets seen. (INS=insulin, AMY=amylase, HO=Hoescht) scale bar is 50 micrometers (E) PDL+ethanol infusion preserves the islets in the ligated tail, while preventing regeneration of exocrine tissue. (F) Sham-operated mice show islets surrounded by exocrine tissue. (G) β-cell mass in the tail is significantly diminished 24-weeks after PDL as compared to sham-operated. Infusion of ethanol at 8-weeks post-PDL prevents β-cell loss. PDL+ethanol-infused mice show no difference in β-cell mass as compared to sham-operated. (H) Insulin secretion by islets from the pancreatic tail is diminished after PDL per 200 islets, with either low or high glucose concentration exposure, compared to sham-operated tail islets. The PDL+ethanol-infused tail islets have a normal insulin secretion pattern compared to sham-operated control islets.

Mouse pancreatic duct ligation (PDL) yields a model that is reflective of chronic pancreatitis with progressive loss of islet tissue. In the PDL procedure, the pancreatic duct is ligated at the mid-point of the pancreas (FIG. 4, right image). Thus, only the distal half (tail) of the pancreas is affected since the ligation is positioned at the mid-point of the duct. Initially (weeks 0-8 after ligation), there is near total destruction of the exocrine ductal and acinar cells in the ligated tail, but with preservation of β-cell mass and glucose tolerance (14-16) (FIG. 4, left and center images). FIGS. 5A-5J demonstrate that twelve weeks after PDL, the distal pancreatic islets are nearly absent (22), likely due to secondary injury stemming from the death of the exocrine cells. FIGS. 5A-5E show insulin staining using DAB, whereas FIGS. 5F-5J show insulin and amylase staining using immunofluorescence (with a Hoescht counterstain for labeling cell nuclei). The condition is thus reflective of chronic pancreatitis-related diabetes. Mice maintain a normal fasting blood glucose level and glucose tolerance, even after 24 weeks of PDL, presumably due to the normal islets in the unligated head of the pancreas (FIGS. 6A-6B). In the absence of ethanol infusion, and similar to our recent study (22), a substantial loss of islets and β-cell mass occurred specifically in the PDL-tail compared with sham-controls (0.11±0.01 milligrams vs 0.72±0.01 milligrams, p<0.05) (FIG. 3G). This islet loss is in line with the islet loss seen in subjects with chronic pancreatitis related diabetes (CPRD).

The mouse PDL model is used to determine whether an ethanol infusion shows a similar exocrine ablation and islet sparing in the setting of chronic pancreatitis, and if this selective exocrine ablation can protect the islets to prevent CPRD. Infusion of ethanol into the distal pancreatic duct (starting at a point just beyond the ligation) at the 8-week time point post-PDL prevents the loss of islets in the pancreatic tail, with no detectable recurrent inflammation and no detectable regeneration of acinar cells (as demonstrated by immunofluorescent staining for insulin and amylase, shown in FIGS. 6D-6F). Jaundice rates are less than 5% (jaundice being an indicator of biliary stricturing and/or obstruction). The β-cell mass in the ligated tail after PDL and ethanol infusion shows no difference from the β-cell mass in the same anatomical distribution (tail) of sham-operated controls (0.61±0.01 milligrams vs 0.72±0.01 milligrams). This preservation of β-cell mass is in contrast to the loss of β-cell mass in the ligated portion of the pancreas after PDL without ethanol infusion (0.11±0.01 milligrams vs 0.61±0.01 milligrams, p<0.05) (FIG. 6G). In vitro GSIS by islets harvested from the tail show that the insulin secretion specifically from the isolated tail is low in the setting of PDL alone (low number of islets, so required pooling of specimens) as compared to the controls or to PDL with ethanol infusion (FIG. 6H). The negative effects of a pancreatitis milieu on β-cell function are well known (17). Taken together, these data show that ethanol infusion at 8 weeks prevents PDL related islet destruction and improves β-cell function, and thus suggest that ethanol infusion may prevent CPRD in humans. Other potential benefits of the ethanol infusion procedure could include decreased chronic pain, fewer pancreatic cancers, and a reduction of the other life-threatening complications of chronic pancreatitis.

Methods

Mouse manipulation: All mouse experiments are approved by the Animal Research and Care Committee at the Children's Hospital of Pittsburgh and the University of Pittsburgh IACUC. C57BL/6 mice are all 10 week-old-males purchased from Jackson Laboratory (Bar Harbor, Me., USA). Pancreatic ductal infusion technique is performed as described (11, 18, 19), however infusion is 100% ethanol at a catheter rate of 10 microliters/min to a total volume of 100 microliters. PDL is performed and validated as previously described (10, 15, 16, 18). Intervention, to prevent β-cell loss following PDL, is performed at 8-weeks post-PDL with 100% ethanol as described above. All groups receive elemental diet to counteract the lack of pancreatic enzymes in the ethanol and PDL models.

Glucose Stimulated Insulin Secretion (GSIS): For in vivo GSIS, after 16-hour overnight fast, 9-month post-ethanol infused, 9-month sham operated, 24-week post-PDL, and 24-week post-PDL/16-week post-ethanol mice receive glucose by intraperitoneal injections (1 milligram/gram as a 10% solution). Blood samples are obtained from tail-tip bleedings and blood glucose levels are measured. Plasma insulin levels are determined by ELISA (ALPCO, Salem, N.H., USA). For in vitro static GSIS, digestion and islet isolation is performed as previously described (15, 16, 18) for each condition. Mouse islets are cultured in Ham's F10 medium (Life Technologies, St. Louis, Mo., USA) supplemented with 0.5% BSA (Sigma-Aldrich, St. Louis, Mo., USA), 2 millimoles/liter glutamine, 2 millimoles/liter calcium, and 5 millimoles/liter glucose at 37 degrees Celsius, 95% air/5% CO2. After overnight culture, 200 islets per condition are transferred to new plates and treated with low glucose (2.8 millimoles/liter) and high glucose (16.7 millimoles/liter) conditions. Islets are pelleted by centrifugation and lysed in acid ethanol for assessment of insulin in media and islets by radioimmunoassay (Linco Research Inc., St. Charles, Mo., USA). Results are reported as insulin secreted (nanograms/milliliter) per hour normalized to number of islets.

Histology and Immunohistochemistry: All pancreas samples are fixed and cryo-protected in 30% sucrose overnight before freezing, as described before (16, 18, 21). Primary antibodies for immunostaining are: guinea pig polyclonal antiinsulin (Dako, Carpinteria, Calif., USA), goat polyclonal anti-glucagon (Santa Cruz Biotechnology, Dallas, Tex., USA), rat polyclonal anti-CD31 (BD Biosciences, San Jose, Calif., USA), and rabbit polyclonal anti-amylase (Santa Cruz Biotechnology, Dallas, Tex., USA). Secondary antibodies for indirect fluorescent staining are Cy2, Cy3, and Cy5-conjugated guinea pig and goat-specific (Jackson ImmunoResearch Labs, West Grove, Pa., USA). Nuclear staining is performed with Hoechst solution (Becton-Dickinson Biosciences). Staining and imaging sections are performed as previously described (16). Histological quantification is performed on the basis of at least 10 sections that are 100 micrometers apart for each mouse. Quantification of β-cell mass is performed as has been previously described (18, 21).

Data analysis: GraphPad Prism 6.0 (GraphPad Software, Inc. La Jolla, Calif.) is used for statistical analyses. All values are depicted as mean±standard error of the mean. Five repeats are analyzed in each condition. All data are statistically analyzed using one-way ANOVA with a Bonferroni correction, followed by Fisher's Exact Test to compare two groups. Significance is considered when $p<0.05$.

Example 2

Retrograde Infusion of Acetic Acid in Mouse Pancreatic Duct

Figure 7:
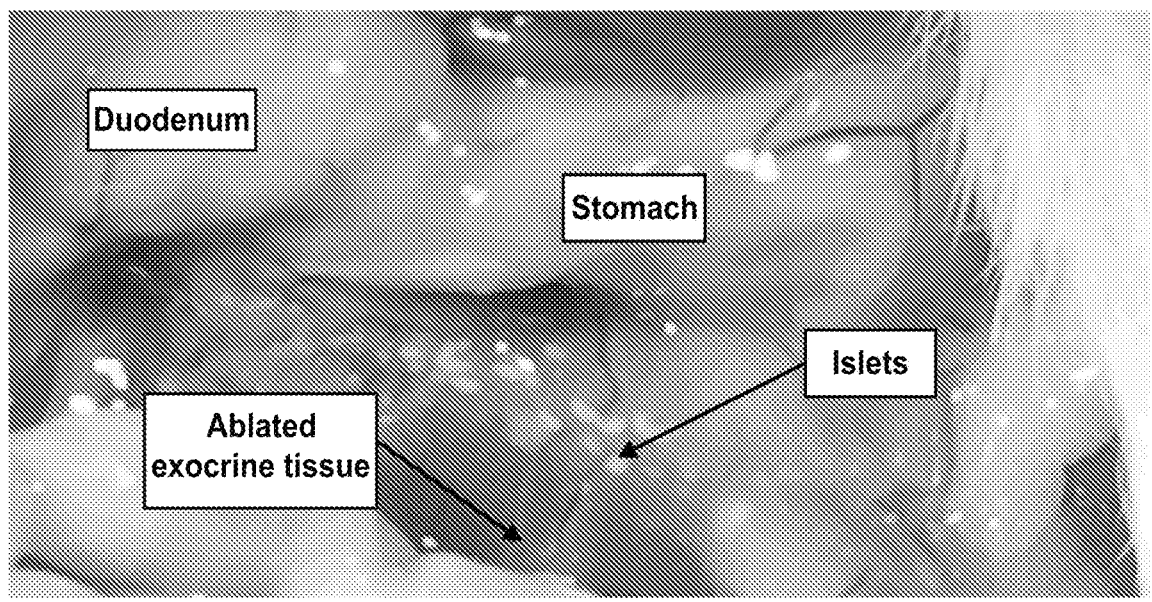
FIG. 7 shows a photograph of a pancreas 6 months after infusion with 1% acetic acid. White islets (marked by arrows) are preserved.
Figure 8A:
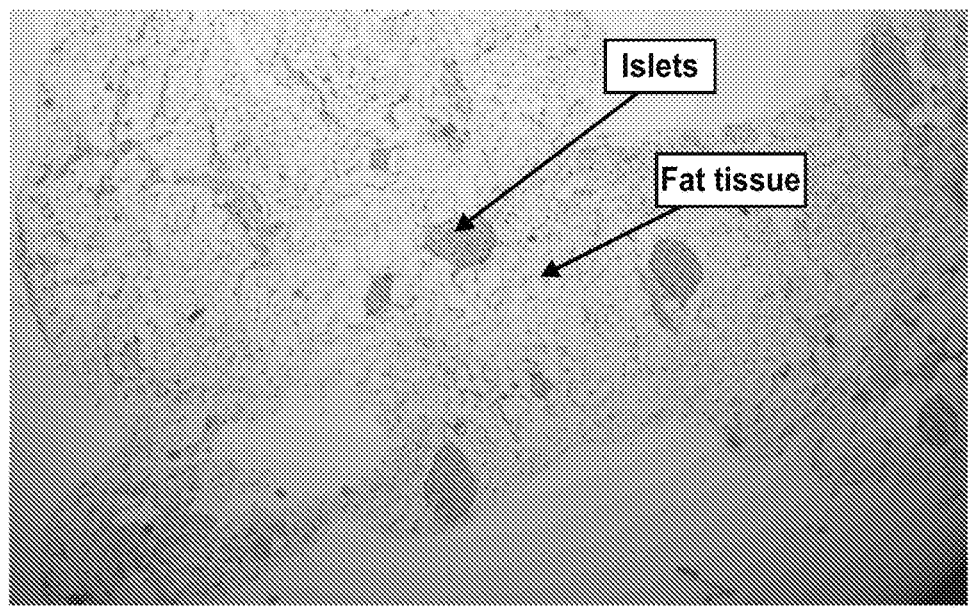
FIGS. 8A-8B show histology and immunohistochemistry of a pancreas treated with 1% acetic acid. (A) Exocrine pancreatic tissue has been replaced with fat cells, but the islets have remained intact. (B) The tissue is insulin positive and amylase negative, indicating that the exocrine tissue has been ablated.
Figure 8B:
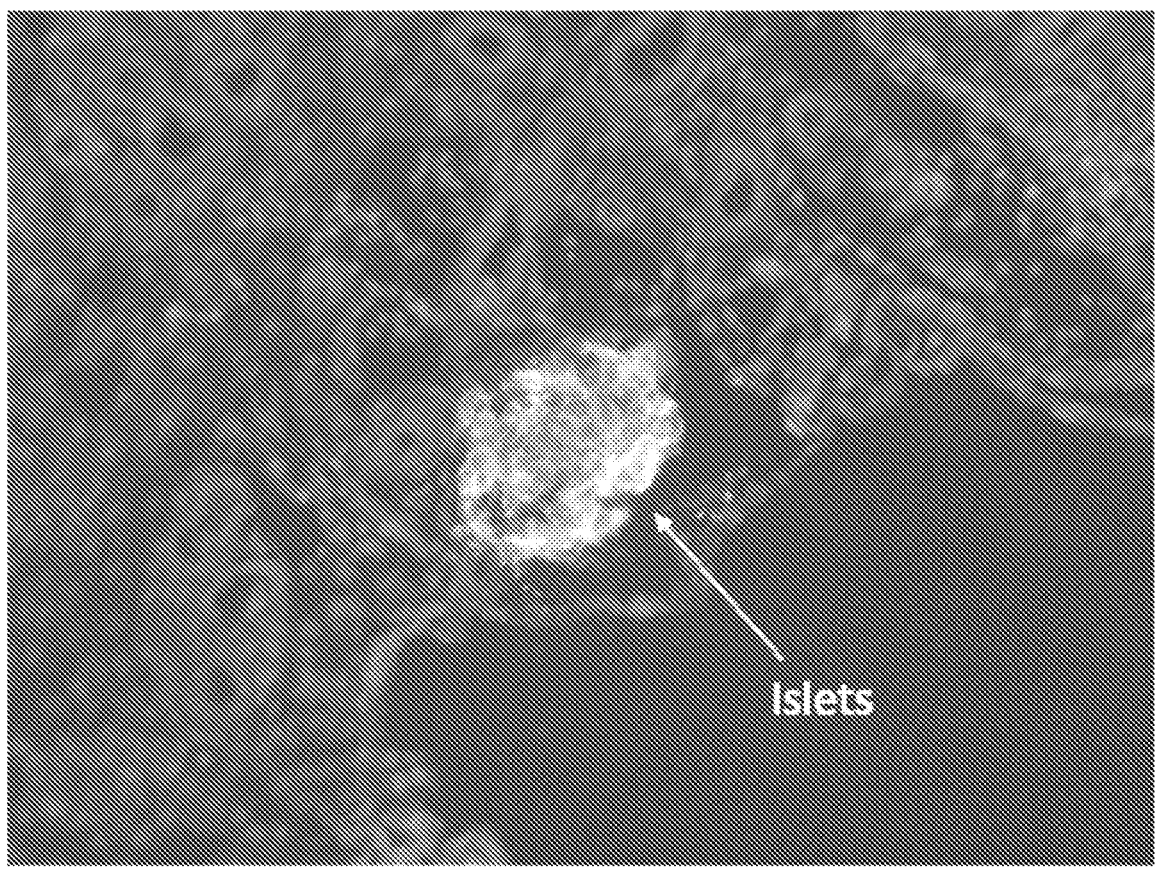
Figure 9A:
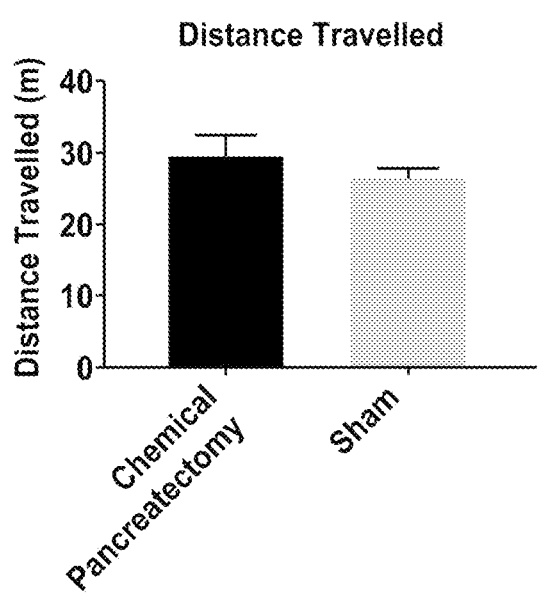
FIGS. 9A-9B show data from behavioral studies that demonstrate that the treatment of mouse pancreas with 1% acetic acid does not cause pain. (A) The distance traveled in meters by mice in the treatment group was not significantly different than the distance traveled by mice in the sham group (B) The rearing, measured in time pressed, was also not significantly different between the treatment and sham groups.
Figure 9B:
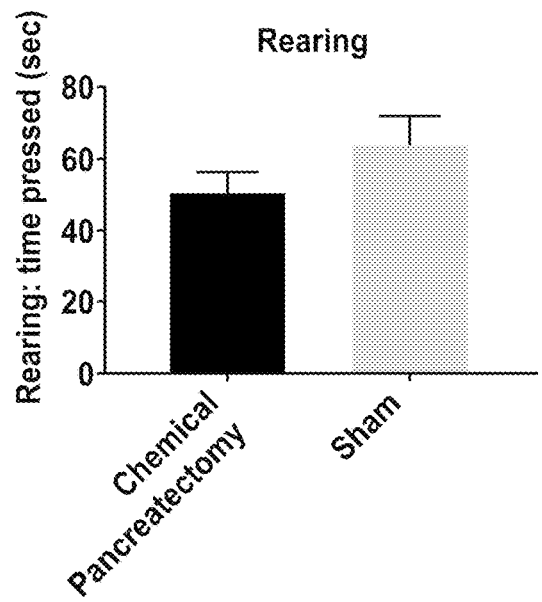

The pancreatic infusion methods described in Example 1 were performed in mice with 1% acetic acid. FIG. 7 shows ablation of the exocrine tissue with visible intact islets, demonstrating that the 1% acetic acid infusion allowed endocrine tissue to be preserved. FIG. 8A shows a histology image of treated pancreatic tissue. Exocrine pancreatic tissue has been replaced with fat cells, but the islets have remained intact. FIG. 8B shows immunohistochemistry of treated pancreatic tissue. The tissue is insulin positive and amylase negative, indicating that the exocrine tissue has been ablated. The mixture of acetic acid and ethanol does not cause diabetes. Fasting glucose levels and glucose tolerance tests show no difference between ethanol infused mice and sham operated controls at all time points. FIGS. 9A and 9B are the results of open field testing, which quantitatively tracks mouse movements in different ways that reflect the degree of pain that they are experiencing. The distance traveled in meters by mice in the treatment group was not significantly different than the distance traveled by mice in the sham group (FIG. 9A). The rearing, measured in time pressed, was also not significantly different between the treatment and sham groups (FIG. 9B). These results demonstrate that the treatment does not cause pain.

Example 3

Retrograde Infusion of Acetic Acid in Cynomologus Pancreatic Duct

Figure 10:
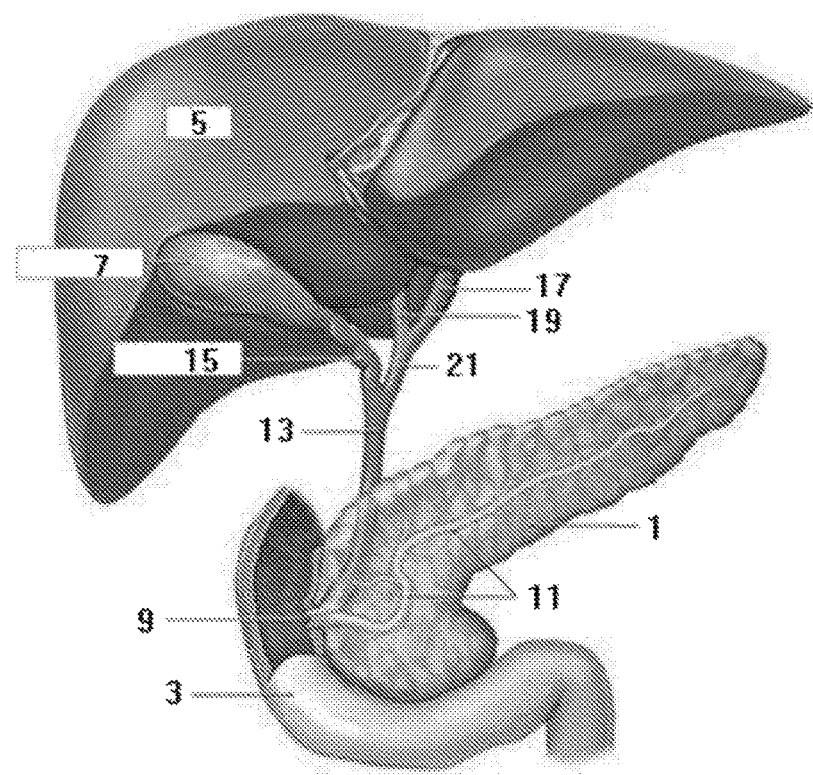
FIG. 10 shows the anatomy of the pancreas and surrounding tissues.

The primate pancreas has a more rigid structure and lower tissue compliance than the mouse pancreas. For reference, FIG. 10 shows an anatomical schematic of the human pancreas 1, duodenum 3, liver 5, ampulla of Vater 9, pancreatic duct 11, bile duct 13, cystic duct 15, left hepatic duct 17, right hepatic duct 19, and common hepatic duct 21.

Cynomologus monkeys can be used to study the retrograde infusion protocol in primates. All procedures are performed in accordance with the regulations specified by the University of Pittsburgh IACUC. The Cynomologus monkeys are first quarantined for 30 days, then transferred to the primate facility and given a 1 to 2-week acclimatization period before operating. After acclimatization, the animals undergo a laparotomy and duodenotomy with cannulation of the ampulla of Vater and temporary clamping of the common bile duct to prevent perfusion of the liver (additional details below).

Figure 11:
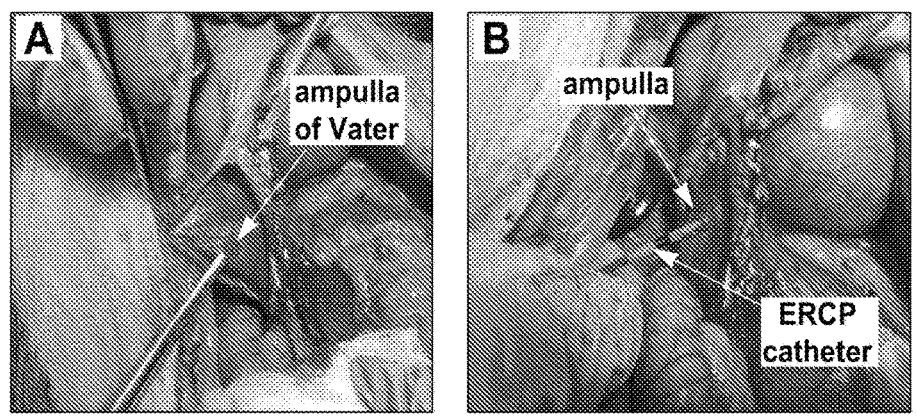
FIG. 11 shows photographs from necropsy of an 8 kg Cynomolgus monkey. (A) Opened duodenum shows the normal location of the opening to the pancreatico-biliary duct (ampulla of Vater) identical to human anatomy. (B) The ERCP catheter is inserted through the ampulla and specifically into the main pancreatic duct. C) Ink injection through the ERCP catheter into the pancreatic duct demonstrates complete perfusion of the entire pancreas (circled dark-stained tissue).

A necropsy of an 8 kilogram Cynomologus monkey demonstrated that the related anatomical structures are similar to humans (FIG. 11). For example, there is a major papilla and a minor papilla. The major papilla drains the bile and most of the pancreatic juice. The common bile duct fuses with the main pancreatic duct (Duct of Wirsung in humans) to form a short common channel (approximately 1-1.5 cm). In FIG. 11A, the location of the ampulla of Vater is visible through the opened duodenum in a position that is similar to the human anatomy. FIG. 11B shows an endoscopic retrograde cholangiopancreatography (ERCP) catheter being inserted through the ampulla of Vater, where it is routed into the main pancreatic duct. FIG. 11C shows the results of an ink injection through the ERCP catheter into the pancreatic duct, demonstrating complete perfusion of the entire pancreas (dark-stained tissue within the oval).

Figure 12A:
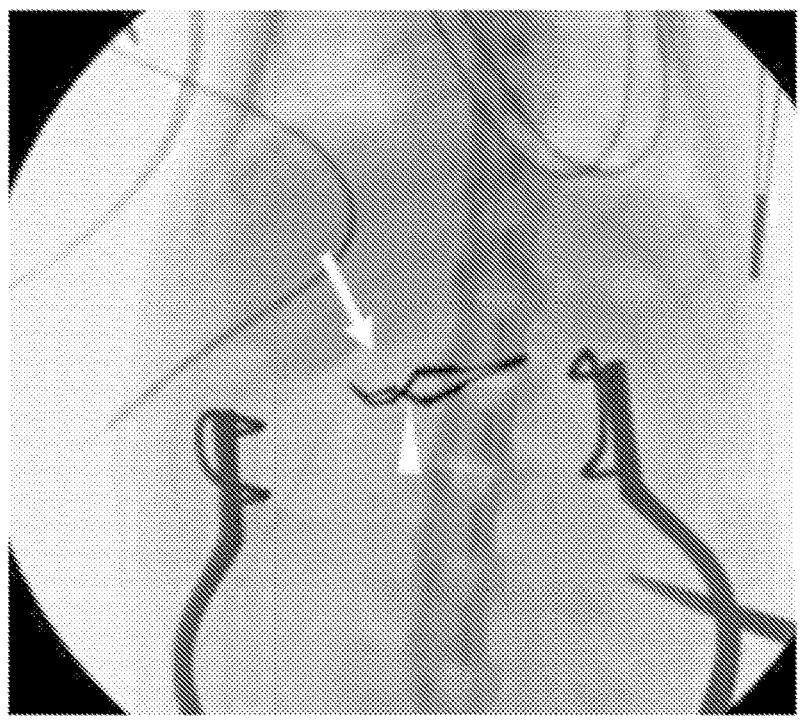
FIGS. 12A-12B show fluoroscopic images during the surgery.
Figure 12B:
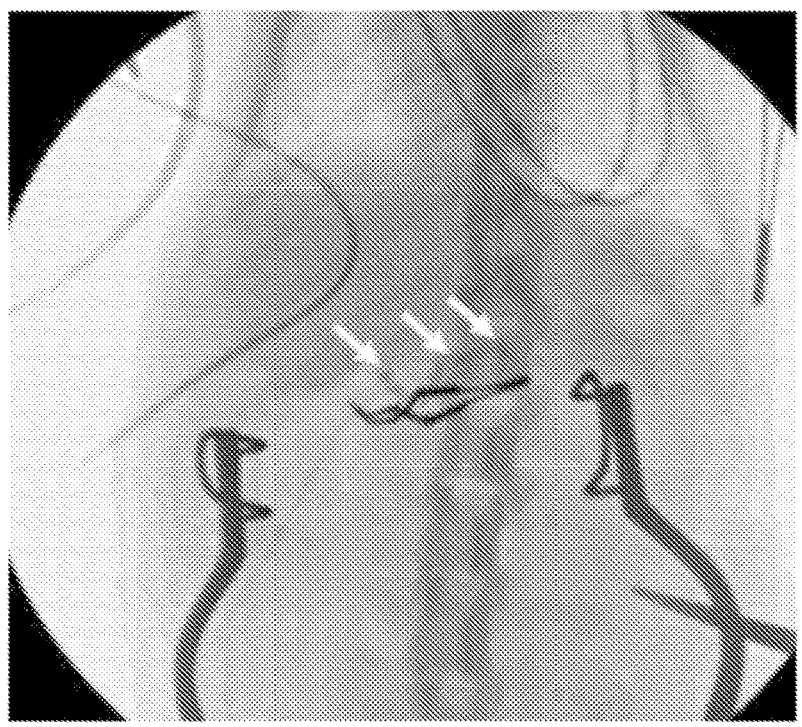
Figure 13:
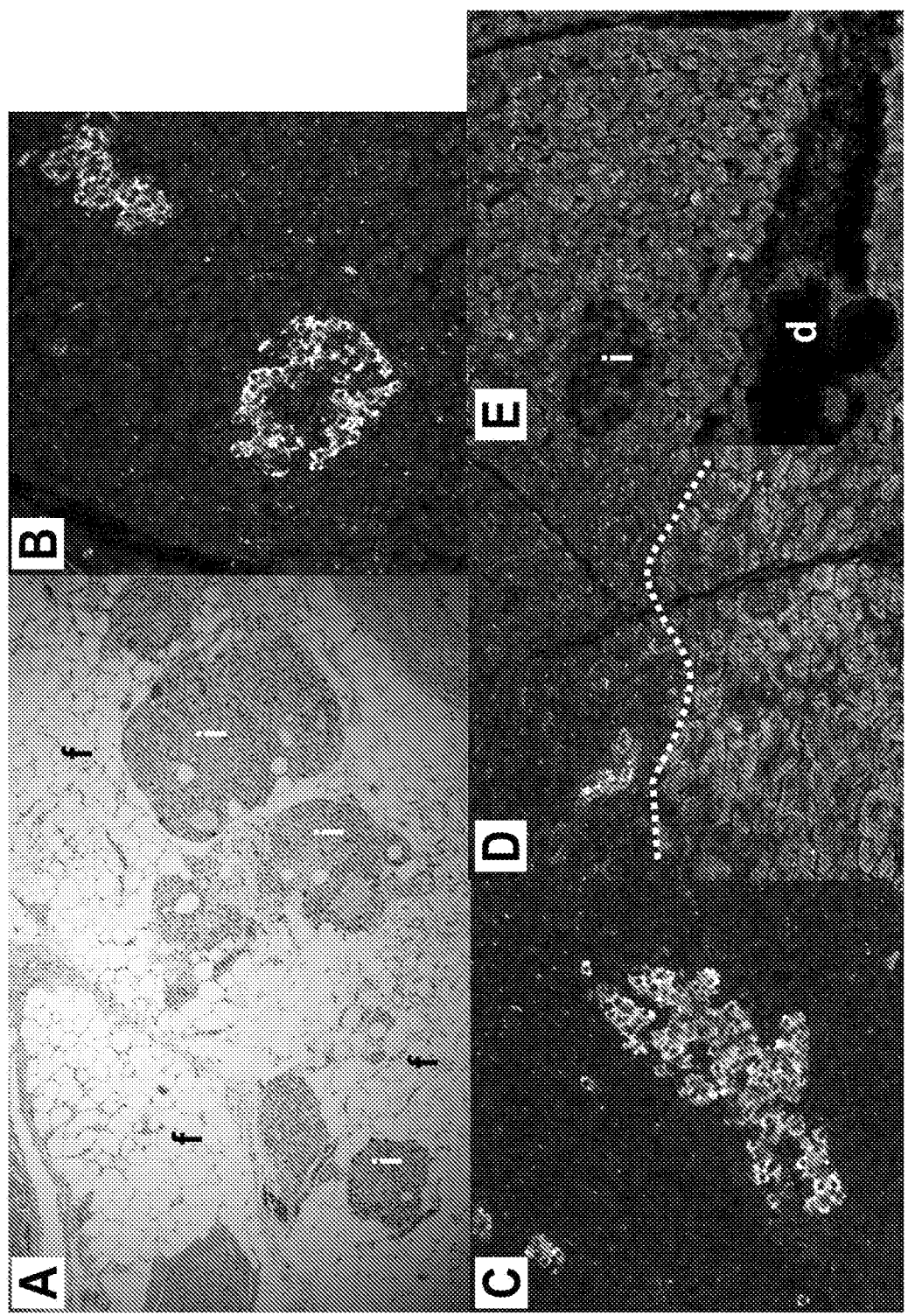
FIGS. 13A-13E show histologic images of a monkey pancreas three weeks after infusion of 1% acetic acid. (A) H&E shows intact islets (i) and fatty degeneration (f) of the exocrine tissue. Immunohistochemistry for insulin (green) and amylase (red) in the pancreatic head (B), body (C), and tail (D), and in a control pancreas from a streptozotocin (insulin-negative islet) treated monkey pancreas (E). d, duct structure. In (D) the transition point where the infusion was inadequate to ablate the exocrine tissue more distally is shown (dotted line).

Acetic acid (1%) is then infused at a specified rate, pressure, and volume via a pressure-regulated infusion pump. For example, an 8 to 9 kilogram Cynomolgus can receive 7 milliliters of 1% acetic acid, at a pressure of 500 centimeters of water. Fluoroscopic dye can also be infused to confirm the location and positioning of the catheter (FIGS. 12A and 12B). The volume and pressure of the infusion can be varied to balance the ablation of the exocrine tissue with the retention of the islet tissue (increasing the volume and/or pressure ablates additional exocrine tissue, whereas decreasing the volume and/or pressures retains additional islet tissue). The catheter and clamp are then removed and the surgery completed. The Cynomolgus monkeys recover well from this procedure.

The pancreas is harvested 3 to 6 weeks later. FIGS. 13A-13E shows histologic images of a monkey pancreas three weeks after infusion of 1% acetic acid. This perfusion resulted in ablation of the exocrine pancreas in the head and body of the pancreas, and part of the tail.

Methods

Cynomologus infusion procedure details: After induction of general anesthesia, the abdomen is prepped and draped and a 10 to 12 centimeter upper abdominal midline incision created. The duodenum is fully mobilized out of the retroperitoneum and a non-crushing clamp applied to the common bile duct to prevent the composition from perfusing the bile duct and liver. A two centimeter duodenotomy is then created to expose the ampulla of Vater, which is cannulated with a 2.8 French double lumen umbilical artery catheter. A clamp is then placed on the minor papilla and catheter to prevent back leaking of the composition. Radio-opaque contrast is then infused into the smaller channel of the catheter under fluoroscopic guidance to confirm filling of the pancreatic duct, and no filling of the bile duct. Once confirmed, the infusion pump is connected to the other channel of the catheter and the pancreas is infused, followed by the 10-minute dwell time with the clamps and catheter left in place. The clamps and catheter are then removed and the duodenum and abdomen closed. This infusion surgery is well tolerated by Cynomologus monkeys.

The pancreas is harvested 3 to 6 weeks later. In some cases, or for some test groups, multiple infusions can be performed over the course of the study to ensure complete ablation of the exocrine pancreatic tissue.

During the 3 to 6-week period between the procedure and the sacrifice, Cynomologus monkeys are supplied with CREON enzymes as a dietary supplement to avoid malabsorption due to loss of acinar enzyme production by the pancreas. Random blood glucose checks are performed two to three times per week to confirm euglycemia. One day prior to sacrifice, a standard oral glucose tolerance test is performed. Throughout the 3 to 6-week period, the Cynomologus monkeys are monitored for scleral icterus as a sign of possible biliary obstruction due to bile duct structuring caused by the infusion.

At harvest, the pancreas and duodenum are examined grossly in situ, and then removed en bloc along with the common bile duct. The common bile duct and ampulla of Vater are opened to inspect for strictures. The pancreas is examined for the presence of intact acinar tissue, which is easily discernible with only simple 2 to 3× loupe magnification. At this time, if the acinar/exocrine tissue is gone, the islets are visible as small white spheres, as shown in FIG. 2A (these islets are not normally visible due to the opaque overlying acinar tissue). The pancreas is then processed for histologic analysis to confirm the presence or absence of acinar tissue and ducts, to confirm the presence of islets, and to confirm normal morphometry of the islets. In addition, beta cell mass is calculated based on the percent insulin positive area on histology along with the gross weight of the pancreas. The experimental values are compared to the normal range for Cynomologus NHP pancreas beta cell mass (12) to determine whether the infusion has decreased beta cell mass significantly.

Example 4

Retrograde Infusion of the Human Pancreatic Duct

The adult human anatomy is larger than that of the Cynomologus, and as such infusions can be delivered by an endoscopic retrograde cholangiopancreatography (ERCP) procedure, described below, with pancreatic duct-specific cannulation. As opposed to clamping the bile duct, which would require laparoscopy or a laparotomy, an occluding mechanism and/or an aspiration element can limit the extent that the infusion enters the biliary tree or other surrounding structures. In some cases, multiple infusions can be performed over time to ensure complete ablation of the exocrine pancreatic tissue. Some human chronic pancreatitis subjects have some degree of ductal obstruction that can change the deliverability of the infusion. These cases are treated with alternative strategies, for example, by laparotomy to access the pancreatic duct and more directly deliver the infusion. Smaller pediatric subjects can also be treated by alternative strategies, such as the laparotomy and duodenotomy described in Example 3, or a variation thereof.

Example 5

Infusion Procedure and Devices for Performing the Same

Figure 14:
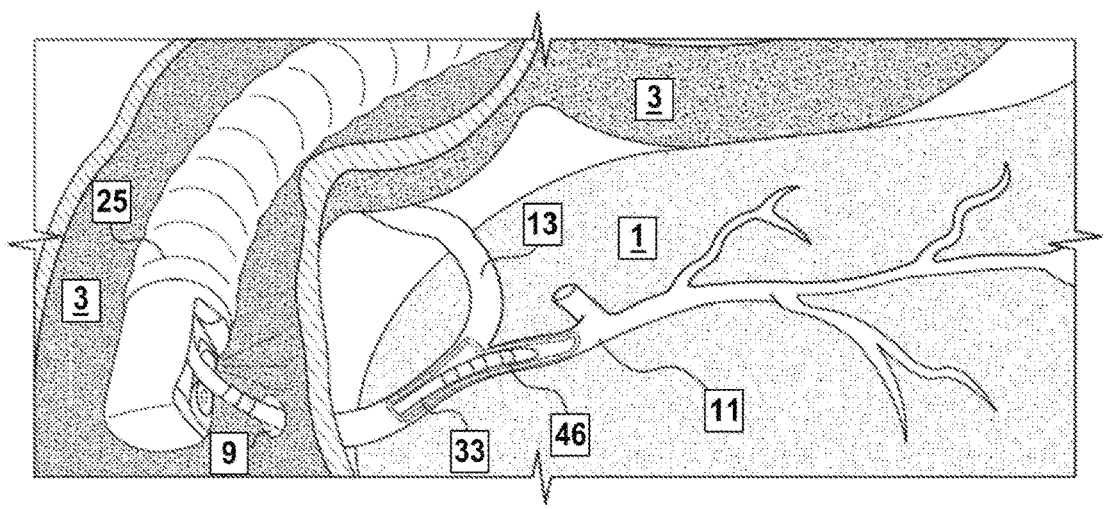
FIG. 14 shows an endoscope in the duodenum of a patient, with the catheter entering the pancreatic duct via the ampulla of Vater.
Figure 15:
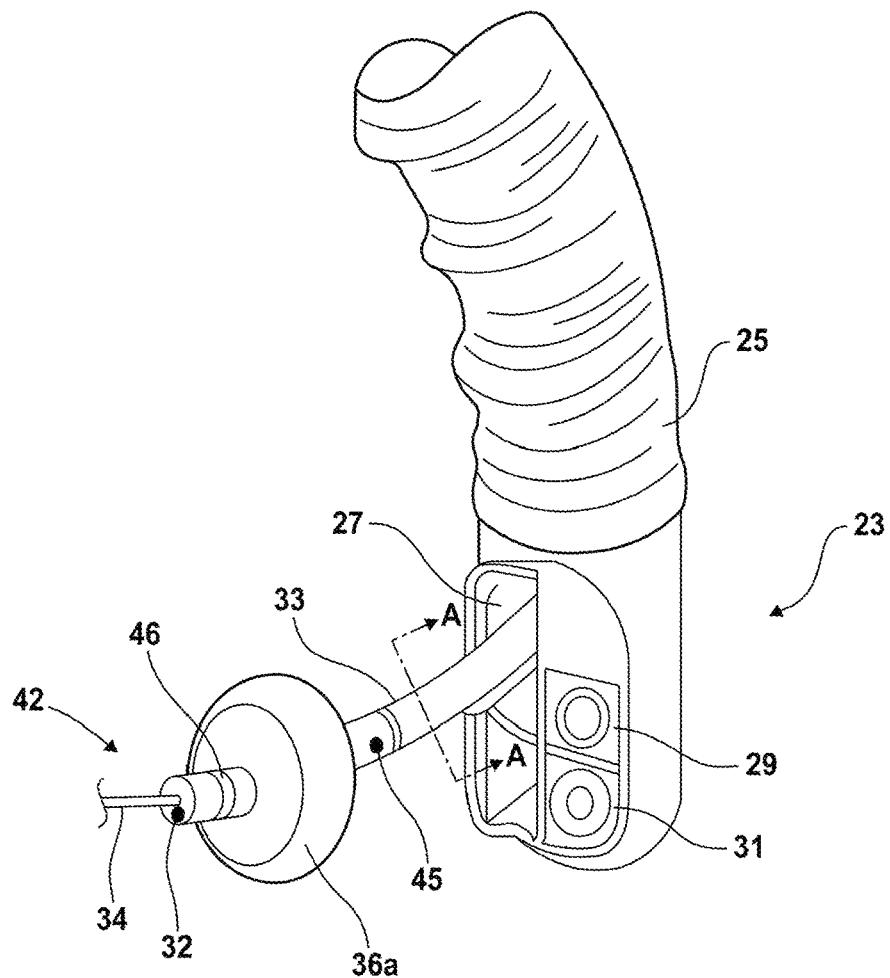
FIG. 15 shows a guidewire and catheter exiting the distal port of an endoscope. The occluding mechanism is activated in this view. Line A-A shows the position of the cross sectional view depicted in FIG. 19.

In some embodiments, the composition may be infused into the pancreatic duct during an ERCP procedure. FIG. 10 displays the relevant anatomy for the following discussion. Briefly, an endoscope, for example, a duodenoscope, is routed through a subject's digestive tract and into the duodenum 3 until it is adjacent with the ampulla of Vater 9. The ampulla of Vater 9 is inspected using the endoscope. As shown in FIG. 14, a catheter 33 (such as the one shown in FIG. 15) is routed through the endoscope 25, out a distal port 27 at a distal portion 23 of the endoscope 25, through the ampulla of Vater 9, and into the pancreatic duct 11. The distal end of the catheter is placed into the pancreatic duct 11, about 1 to 2 centimeters from the proximal end of the pancreatic duct 11, as shown in FIG. 14. The catheter can deliver a contrast liquid, for example, a radiopaque dye, into the pancreatic duct 11 for visualization by an imaging system, for example, a fluoroscopic imaging system. As shown in FIG. 15, the distal portion of the catheter can include an occluding system that includes an occluding mechanism 36, which is activated to seal the proximal portion of the pancreatic duct 11 prior to infusion of the composition. This limits the extent that the composition can escape the pancreatic duct 11 to contact and thus damage the biliary tree or the duodenum 3. The distal portion of the catheter 33 can also (or alternatively) include an aspiration system that creates a negative suction to remove proximally travelling fluid through aspiration port 45, further limiting the extent that the composition can leak into the biliary tree or the digestive tract. In some embodiments, the composition is completely prevented from entering tissue structures other than the pancreatic duct by the occluding mechanism 36, the aspiration port 45, or a combination thereof. Once the occluding mechanism 36 and/or aspiration port 45 are activated, pressurized fluid is delivered to the pancreatic duct 11 via infusion fluid port 32. The occluding mechanism 36 and/or aspiration port(s) 45 are then deactivated, the catheter 33 retracted back into the endoscope 25, and the endoscope 25 is retracted from the subject.

FIG. 15 shows the distal portion 23 of an endoscope 25. The endoscope 25 can include a distal port 27, a camera 29, and a light 31. Catheter 33 exits the endoscope via distal port 27, and may be routed over guidewire 34 for steering purposes. An occluding mechanism 36 is used to limit the extent that the composition can leak proximally during the procedure. In some embodiments, the occluding mechanism 36 is positioned less than 50 millimeters from the distal end of the catheter 33, including less than 50, less than 40, less than 30, and less than 20 millimeters from the distal end of the catheter 33. For example, the occluding mechanism can be placed from 5 to 15 millimeters proximal to the distal end of the catheter 33. The occluding mechanism 36 can be joined to the catheter 33, or it can be a separate component from the catheter 33. In the embodiment shown in FIG. 15, the occluding mechanism 36a is a balloon that can contact the walls of the pancreatic duct 11 to prevent backflow of the composition.

Figure 16:
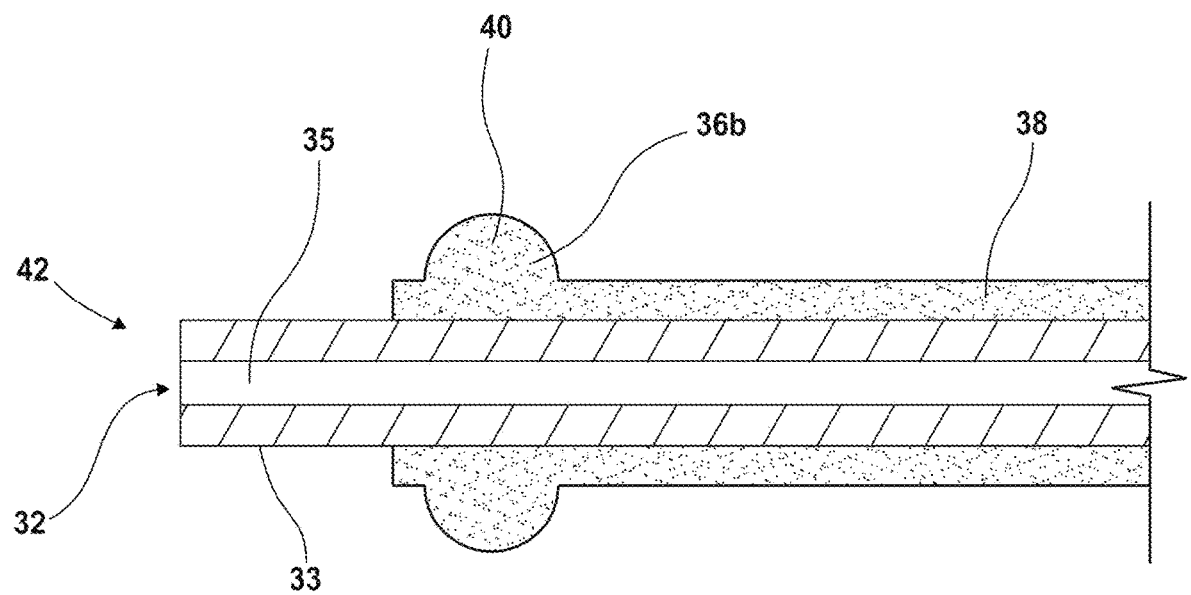
FIG. 16 shows a cross sectional view of a sheath extended over a catheter and including a bulbous distal portion that creates an occluding mechanism.

In other embodiments, such as those shown in FIGS. 16, 17A-B, and 18, the occluding mechanism 36 can be a sheath 38 that extends over part or all of the catheter 33. For example, the sheath 38 shown in FIG. 16 has a distal portion 40 with a bulbous shape. The occluding mechanism 36b is the bulbous shaped distal portion 40 of the sheath, which is advanced toward the distal portion 42 of the catheter 33 after the placement of the catheter 33 within the pancreatic duct 11, and before the infusion begins. The sheath 38 may be advanced toward the distal portion 42 of the catheter 33 by the practitioner performing the procedure pushing it forward, for example. The embodiment depicted in FIG. 16 shows a distal portion 40 with a bulbous shape, but in other embodiments, the distal portion 40 can be tapered, widening as it extends proximally away from the distal portion 40 of the sheath 38. Alternatively, the distal portion 40 can include two tapered regions (proximal and distal tapered regions) that meet together at their widest points, creating a widest region of the sheath 38 that can contact the walls of a pancreatic duct 11 to limit or prevent backflow of fluid into nearby structures. The proximal tapered region of the distal portion 40 of the sheath 38 narrows as it extends proximally away from the distal portion 40 of the sheath 38, and the distal tapered region of the distal portion 40 of the sheath 38 narrows as it extends distally toward the distal end of the sheath 38.

Figure 17A:
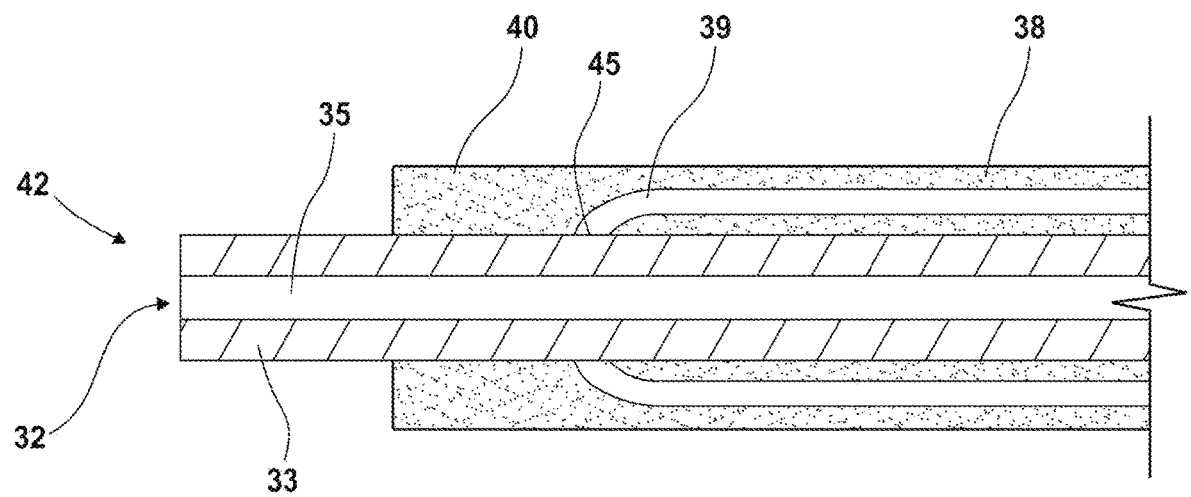
FIGS. 17A and 17B show a cross sectional view of a sheath extended over a catheter and having an expandable cup shaped distal portion that creates an occluding mechanism.
Figure 17B:
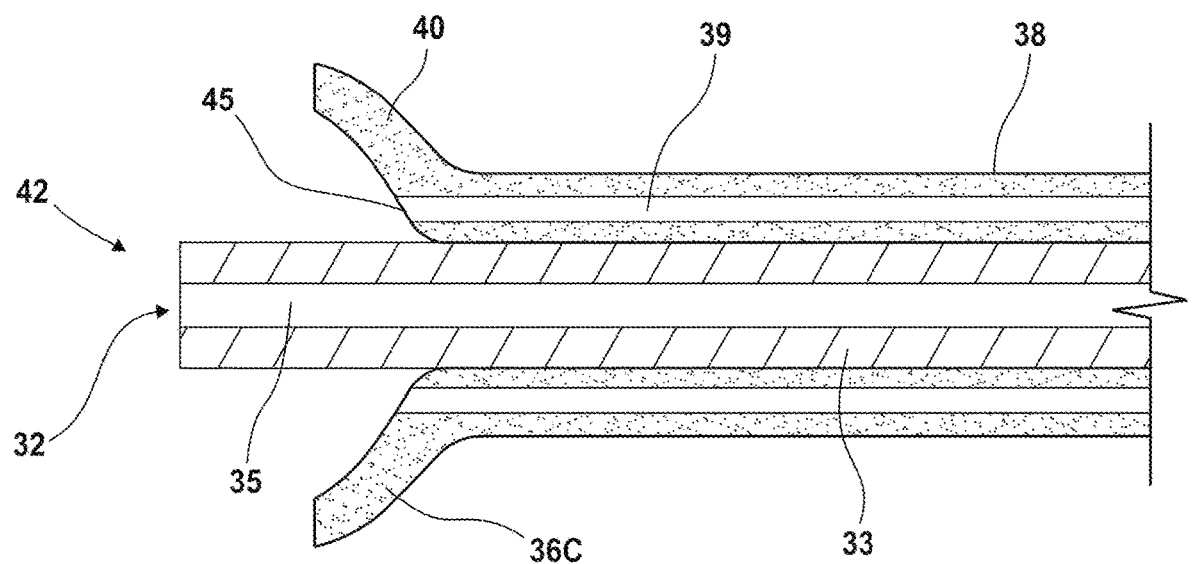

In other embodiments, such as the one shown in FIGS. 17A and 17B, the distal portion 40 of sheath 38 is shaped like a cup or a funnel, flaring outward and away from the catheter 33 in a distal direction to create an occluding mechanism 36c. The distal portion 40 of the sheath 38 in a cup or funnel shaped embodiment could be advanced in a collapsed state (FIG. 17A), then activated and expanded once positioned near the distal portion 42 of the catheter 33 (FIG. 17B). The distal portion 40 of the sheath 38 can be embedded with expansion elements, for example, with rods or struts made of a shape memory metal or a shape memory polymer. In other embodiments, the expansion elements can be remotely activated, either electronically, magnetically, or via an occluding system wire that extends proximally to a practitioner performing the procedure and longitudinally through or on a surface of, for example, the catheter 33 and/or the sheath 38. The expansion elements could be configured to expand when the physician creates or relieves the tension in the occluding system wire.

Figure 18:
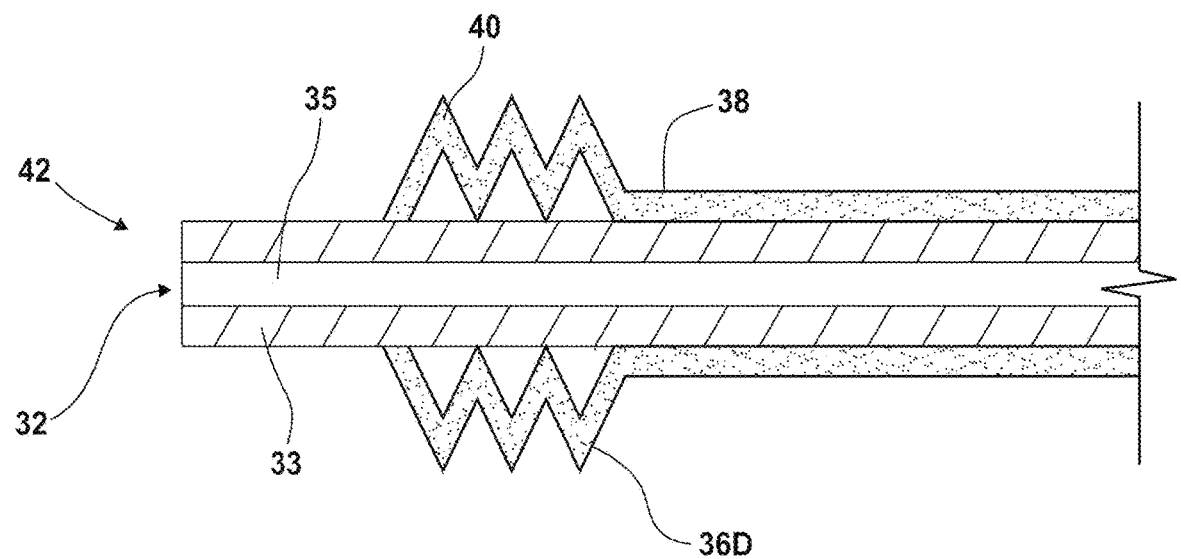
FIG. 18 shows a cross sectional view of a sheath extended over a catheter, with its distal portion pulled back into an accordion-like structure that creates an occluding mechanism.

In other embodiments, such as the one shown in FIG. 18, the distal portion 40 of sheath 38 can be positioned near or over the distal portion 42 of the catheter 33 during advancement through the ampulla of Vater 9 and the pancreatic duct 11. Once positioned, the distal portion 40 of sheath 38 can be pulled back from the distal portion 42 of the catheter 33 to create an occluding mechanism 36d, which is an accordion-like structure. The sheath could be pulled back, for example, using an occluding system wire (not shown) that extends proximally through or on the surface of the catheter 33 and/or the sheath 38 and attaches at the distal portion 40. The occluding system wire could, for example, be loosely woven through the distal portion 40 of sheath 38 in a longitudinal direction, such that the distal portion 40 is folded into the accordion-like structure 36d when the occluding system wire is placed under tension. Alternatively, or in combination, the distal portion 40 of the sheath could include circumferentially extending scorings that weaken the distal portion 40 in designated places to ease the folding of the distal portion 40 into the accordion-like structure 36d. Alternatively, proximal portions of sheath 38 can be thicker than the distal portion 40 to limit the folding to the distal portion 40 of the sheath 38.

In some embodiments, the occluding mechanism could be an increase of size of part of the distal portion 42 of the catheter 33. For example, the distal portion 42 could include a swelling material located inside the catheter wall, or on its external surface. The swelling material could be activated, for example, electronically, magnetically, or chemically, for example, by detection of a chemical in the infusion fluid, and/or detection of the contrast fluid.

Multiple occluding mechanisms discussed above may be combined in any configuration that will limit the backflow of the composition out of the pancreatic duct.

In some embodiments, an aspiration element 45 is provided as part of the catheter 33. As shown in FIG. 15, the aspiration element 45 can be an aspiration port leading to an aspiration lumen 39, such as the one shown in the cross sectional diagram of FIG. 19. In other embodiments, the aspiration element can extend outwardly from the surface of the catheter 33. The aspiration element 45 can be located proximally or distally to the occluding mechanism 36. In some embodiments, both the aspiration element 45 and the occluding mechanism 36 are located on the same component. For example, sheath 38, which can provide an occluding mechanism 36 by way of, for example, a bulbous or tapered distal portion 36b, an expandable cup or funnel shaped distal portion 36c, or accordion-like structure 36d, could also incorporate an aspiration element 45 by way of an aspiration port and an aspiration lumen 39, as shown in FIGS. 17A and 17B. As such, the aspiration lumen 39 can be located within the catheter 33, or within sheath 38. In some embodiments, the aspiration element 45 is used alone, instead of an occluding mechanism 36.

Figure 19:
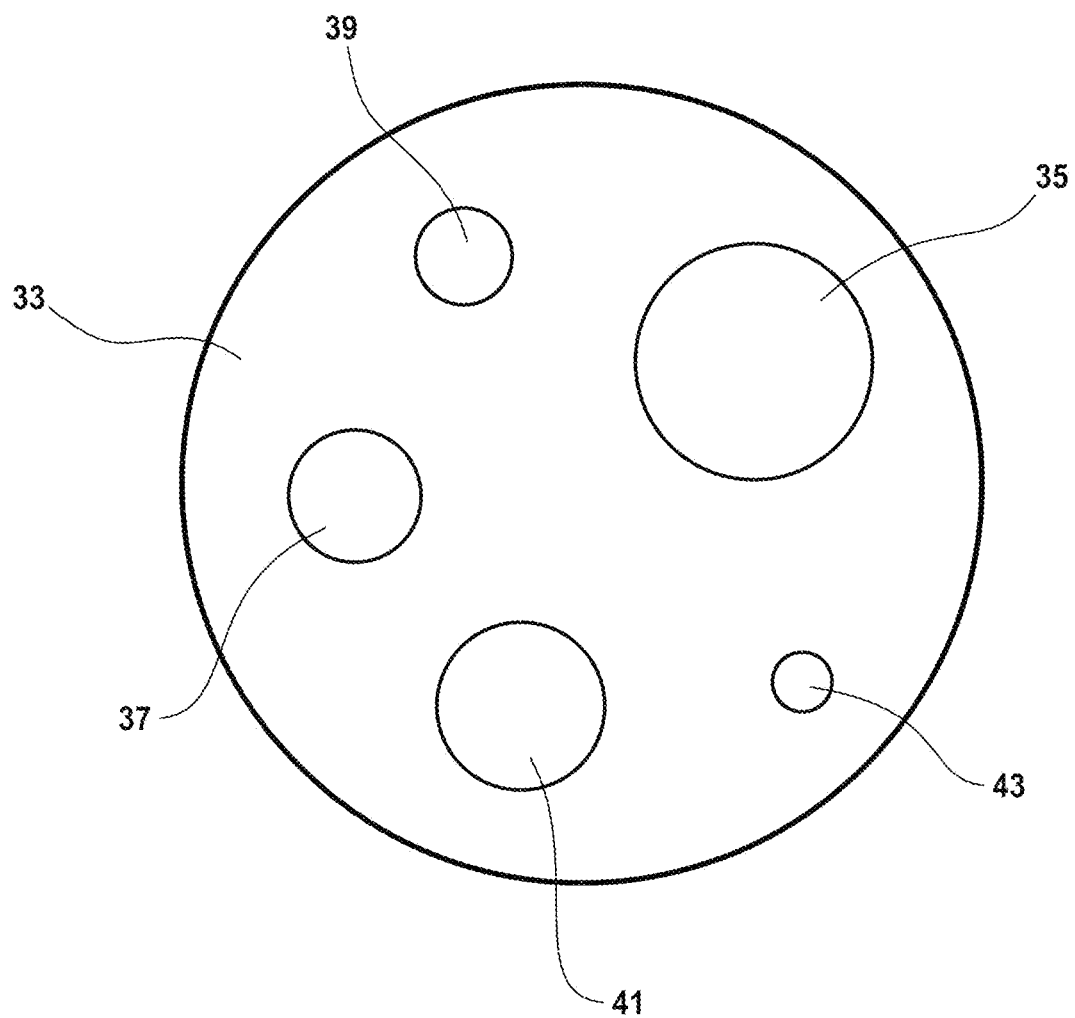
FIG. 19 shows a cross sectional view of the catheter taken along the lines A-A of FIG. 10.

FIG. 19 is a cross sectional diagram of an embodiment of catheter 33 having multiple lumens. The cross section is taken across lines A-A of FIG. 15. The composition is delivered via an infusion system that includes a first infusion lumen 35. The composition exits the infusion lumen 35 via an infusion fluid port 32 at the distal portion 42 of the catheter 33. A contrast fluid delivery system can deliver contrast fluid via the first lumen 35 (which is shared with the infusion system), or via a second, separate contrast fluid lumen 37. The contrast fluid exits the first or second lumen via a port at the distal portion 42 of the catheter 33, which may be the same port that is used to deliver the composition, or it may be a separate port in communication with a separate contrast fluid lumen.

Referring still to FIG. 19, if an aspiration system is included, it will include a lumen to carry aspirated fluid. The aspirated fluid can share the second lumen 37 with the contrast fluid delivery system of the catheter 33, or the aspiration system can have a third, separate aspiration lumen 39. The aspirated fluid enters the aspiration lumen 39 at an aspiration element 45 that is located on the distal portion 42 of the catheter 33 (as shown in FIG. 15), or, as shown in FIGS. 17A and 17B, at the distal portion 40 of sheath 38.

Alternatively, or in addition, the occluding system may utilize/share the second or third lumens 37, 39 and ports with the contrast fluid delivery or the aspiration systems, or the occluding system may include its own, separate, occluding system lumen 41. The occluding system lumen 41 may be placed into fluid communication with, for example, a balloon occluding mechanism 36a, such as the one shown in FIG. 15. Alternatively, the occluding system lumen 41 may house an occluding system wire that is used to advance, retract, and/or otherwise expand the distal portion 40 of sheath 38 of the embodiments shown in FIGS. 17-18 to manipulate occluding mechanisms 36c or 36d. The catheter can also include one or more wire lumens 43 for housing guidewires and/or steering wires, which exit via one or more steering/guidewire exit ports on the sheath. The steering/guidewire exit ports may be located on the distal portion of the sheath, or they may be located proximally to the distal portion of the sheath.

The catheter can include one or more fluoroscopic markings 46, as shown in FIGS. 14 and 10, such that it may be visualized as it is routed through the ampulla of Vater and into the pancreatic duct under fluoroscopic guidance. The distal end of the catheter 33 can be bent by steering wires or guidewire(s) that extend through wire lumen(s) 31. If a guidewire 34 is used, it can be routed into the pancreatic duct in advance of the catheter to guide the catheter 33 into place.

The infusion system can include a pressure regulator to modulate the pressure of the infusion fluid that enters the proximal portion of the catheter 33. The pressure regulator can be tuned by the practitioner performing the procedure. Gauges can also be included to measure the flow rate and the volume of fluid that has been infused.

Unless defined otherwise, all technical and scientific terms used herein have the same meanings as commonly understood by one of skill in the art to which the disclosed invention belongs. Publications cited herein and the materials for which they are cited are specifically incorporated by reference.

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims. Those skilled in the art will recognize, or be able to ascertain using no more than routine experimentation, many equivalents to the specific embodiments of the invention described herein. Such equivalents are intended to be encompassed by the following claims.

REFERENCES

1. Yadav D, Timmons L, Benson J T, Dierkhising R A, Chari S T., Incidence, prevalence, and survival of chronic pancreatitis: a population-based study. Am J Gastroenterol. 2011 December; 106(12):2192-9.
2. Levy P, Dominguez-Mufioz E, Imrie C, Lohr M, Maisonneuve P. Epidemiology of chronic pancreatitis: burden of the disease and consequences. United European Gastroenterol J. 2014 October; 2(5):345-54.
3. Uc A, Andersen D K, Bellin M D, Bruce J I, Drewes A M, Engelhardt J F, Forsmark C E, Lerch M M, Lowe M E, Neuschwander-Tetri B A, O'Keefe S J, Palermo T$_M$, Pasricha P, Saluja A K, Singh V K, Szigethy E M, Whitcomb D C, Yadav D, Conwell D L. Chronic Pancreatitis in the 21st Century—Research Challenges and Opportunities: Summary of a National Institute of Diabetes and Digestive and Kidney Diseases Workshop. Pancreas. 2016 November; 45(10):1365-1375.
4. Kelly A, Moran A. Update on cystic fibrosis-related diabetes. J Cyst Fibros. 2013 July; 12(4):318-31.
5. Bridges N. Diabetes in cystic fibrosis. Paediatr Respir Rev. 2013 May; 14 Suppl 1:16-8.
6. Stram M, Liu S, Singhi A D. Chronic Pancreatitis. Surg Pathol Clin. 2016, December; 9(4):643-659.
7. Hafezi-Nejad N, Singh V K, Johnson S I, Makary M A, Hirose K, Fishman E K, Zaheer A. Surgical approaches to chronic pancreatitis: indications and imaging findings. Abdom Radiol (NY). 2016 October; 41(10):1980-96.
8. Bellin M D, Freeman M L, Gelrud A, Slivka A, Clavel A, Humar A, Schwarzenberg S J, Lowe M E, Rickels M R, Whitcomb D C, Matthews J B; PancreasFest Recommendation Conference Participants, Amann S, Andersen D K, Anderson M A, Baillie J, Block G, Brand R, Chari S, Cook M, Cote G A, Dunn T, Frulloni L, Greer J B, Hollingsworth M A, Kim K M, Larson A, Lerch M M, Lin T, Muniraj T, Robertson R P, Sclair S, Singh S, Stopczynski R, Toledo F G, Wilcox C M, Windsor J, Yadav D. Total pancreatectomy and islet autotransplantation in chronic pancreatitis: recommendations from PancreasFest. Pancreatology. 2014 January-February; 14(1):27-35.
9. Delaune V, Berney T, Lacotte S, Toso C. Intraportal islet transplantation: the impact of the liver micro-environment. Transpl Int. 2017 Jan. 21.
10. Riff B P, Chandrasekhara V. The Role of Endoscopic Retrograde Cholangiopancreatography in Management of Pancreatic Diseases. Gastroenterol Clin North Am. 2016 March; 45(1):45-65.
11. Xiao X, Guo P, Prasadan K, Shiota C, Peirish L, Fischbach S, Song Z, Gaffar I, Wiersch J, El-Gohary Y, Husain S Z, Gittes G K. Pancreatic cell tracing, lineage tagging and targeted genetic manipulations in multiple cell types using pancreatic ductal infusion of adeno-associated viral vectors and/or cell-tagging dyes. Nat Protoc. 2014 December; 9(12):2719-24.
12. Saisho Y, Butler A E, Manesso E, Galasso R, Zhang L, Gurlo T, Toffolo G M, Cobelli C, Kavanagh K, Wagner J D, Butler P C. Relationship between fractional pancreatic beta cell area and fasting plasma glucose concentration in monkeys. Diabetologia. 2010 January; 53(1):111-4.
13. Raimondi S, Lowenfels A B, Morselli-Labate A M, Maisonneuve P, Pezzilli R. Pancreatic cancer in chronic pancreatitis; aetiology, incidence, and early detection. Best Pract Res Clin Gastroenterol. 2010; 24(3):349-358.
14. Pan F C, Bankaitis E D, Boyer D, et al. Spatiotemporal patterns of multipotentiality in Ptfla-expressing cells dur- 15. Xiao X, Chen Z, Shiota C, et al. No evidence for beta cell neogenesis in murine adult pancreas. J Clin Invest. 2013; 123(5):2207-2217.
16. Xiao X, Wiersch J, El-Gohary Y, et al. TGFbeta receptor signaling is essential for inflammation-induced but not beta-cell workload-induced beta-cell proliferation. Diabetes. 2013; 62(4):1217-1226.
17. Levy P, Dominguez-Munoz E, Imrie C, Lohr M, Maisonneuve P. Epidemiology of chronic pancreatitis: burden of the disease and consequences. United European Gastroenterol J. 2014; 2(5):345-354.
18. Xiao X, Gaffar I, Guo P, et al. M2 macrophages promote beta-cell proliferation by upregulation of SMAD7. Proc Natl Acad Sci USA. 2014; 111 (13):E1211-1220.
19. Xiao X, Prasadan K, Guo P, et al. Pancreatic duct cells as a source of VEGF in mice. Diabetologia. 2014; 57(5): 991-1000.
20. Xiao X, Guo P, Shiota C, et al. Neurogenin3 activation is not sufficient to direct duct-to-beta cell transdifferentiation in the adult pancreas. J Biol Chem. 2013; 288(35): 25297-25308.
21. Xiao X, Guo P, Chen Z, et al. Hypoglycemia reduces vascular endothelial growth factor A production by pancreatic beta cells as a regulator of beta cell mass. J Biol Chem. 2013; 288(12):8636-8646.
22. Song Z, Fusco J, Zimmerman R, Fischbach S, Chen C, Ricks D M, Prasadan K, Shiota C, Xiao X, Gittes G K. Epidermal Growth Factor Receptor Signaling Regulates β Cell Proliferation in Adult Mice. J Biol Chem. 2016 Oct. 21; 291(43):22630-22637.

The invention claimed is:

1. A method of treating pancreatitis in a subject, the method comprising;
   advancing a distal portion of a catheter into a pancreatic duct of the subject,
   delivering an effective amount of a composition comprising ethanol and/or acetic acid to the pancreatic duct via the catheter at an effective infusion pressure, wherein the amount and infusion pressure are effective to decrease the secretion of digestive enzymes from one or more exocrine tissues of the pancreas, and
   limiting backflow of the composition out of the pancreatic duct.

2. The method of claim 1, further comprising advancing a distal portion of the catheter through an ampulla of Vater and into a pancreatic duct of the subject.

3. The method of claim 1, further comprising advancing an endoscope through an esophagus, a stomach, and a duodenum of the subject and advancing the catheter out a distal port of the endoscope and through the ampulla of Vater.

4. The method of claim 1, further comprising advancing a guidewire into a pancreatic duct and advancing the catheter over the guidewire.

5. The method of claim 1, further comprising creating tension on a steering wire that attaches to the distal portion of the catheter, and steering the catheter into the pancreatic duct.

6. The method of claim 1, wherein the composition comprises ethanol in a concentration of from 40% to 70%.

7. The method of claim 1, wherein the composition comprises acetic acid in a concentration of from 0.1% to 5%.

8. The method of claim 1, wherein the effective amount of the composition is from 3 milliliters to 50 milliliters.

9. The method of claim 1, wherein the effective infusion pressure is from 100 centimeters to 2000 centimeters of water.

10. The method of claim 1, further comprising infusing a contrast fluid into the pancreatic duct and visualizing the location of the catheter.

11. The method of claim 1, further comprising modulating the effective infusion pressure while the catheter is in the pancreatic duct.

12. The method of claim 1, wherein limiting backflow of the composition out of the pancreatic duct comprises limiting backflow of the composition from the pancreatic duct into a biliary tree, an ampulla of Vater, and/or a duodenum.

13. The method of claim 1, wherein limiting backflow of the composition further comprises activating one or both of an occluding mechanism and/or an aspiration system.

14. The method of claim 13, wherein activating an occluding mechanism comprises pushing a fluid through an occluding mechanism lumen of the catheter and inflating a balloon.

15. The method of claim 13, wherein activating an occluding mechanism comprises increasing the size of a distal portion of the catheter.

16. The method of claim 13, wherein activating an occluding mechanism comprises advancing or retracting a distal portion of a sheath over the catheter.

17. The method of claim 13, wherein activating an aspiration system comprises creating a negative pressure in an aspiration lumen of the catheter.

18. The method of claim 13, wherein limiting backflow of the composition further comprises maintaining activation of an occluding mechanism for a dwell time of from 3 to 30 minutes.

19. The method of claim 18, wherein limiting backflow of the composition further comprises maintaining activation of an occluding mechanism for a dwell time of from 5 to 15 minutes.

20. The method of claim 1, wherein the backflow is limited for a time between from 3 to 30 minutes.

* * * * *